(12) United States Patent
Harrison et al.

(10) Patent No.: US 11,607,223 B2
(45) Date of Patent: Mar. 21, 2023

(54) MAGNETIC DEVICES, SYSTEMS, AND METHODS

(71) Applicant: The Regents of the University of California, Oakland, CA (US)

(72) Inventors: Michael R. Harrison, San Francisco, CA (US); Dillon A. Kwiat, San Francisco, CA (US); Richard J. Fechter, San Rafael, CA (US)

(73) Assignee: The Regents of the University of California, Oakland, CA (US)

(*) Notice: Subject to any disclaimer, the term of this patent is extended or adjusted under 35 U.S.C. 154(b) by 130 days.

(21) Appl. No.: 16/625,050

(22) PCT Filed: Jun. 28, 2018

(86) PCT No.: PCT/US2018/040129
§ 371 (c)(1),
(2) Date: Dec. 20, 2019

(87) PCT Pub. No.: WO2019/006194
PCT Pub. Date: Jan. 3, 2019

(65) Prior Publication Data
US 2020/0138438 A1 May 7, 2020

Related U.S. Application Data

(60) Provisional application No. 62/527,690, filed on Jun. 30, 2017.

(51) Int. Cl.
*A61B 17/11* (2006.01)
*A61B 17/00* (2006.01)

(52) U.S. Cl.
CPC . *A61B 17/1114* (2013.01); *A61B 2017/00477* (2013.01); *A61B 2017/00876* (2013.01);
(Continued)

(58) Field of Classification Search
CPC ...... A61B 17/1114; A61B 2017/00477; A61B 2017/00876; A61B 2017/1107;
(Continued)

(56) References Cited

U.S. PATENT DOCUMENTS 2,990,615 A   7/1961  Ohler
3,005,458 A   10/1961 Brook et al.
(Continued)

FOREIGN PATENT DOCUMENTS

CN   101869498 A   10/2010
CN   101889884 A   11/2010
(Continued)

OTHER PUBLICATIONS

PCT International Search Report and Written Opinion dated Aug. 29, 2018 issued in PCT/US2018/040129.
(Continued)

*Primary Examiner* — Jocelin C Tanner
(74) *Attorney, Agent, or Firm* — Christian D. Scholz; Weaver Austin Villeneuve & Sampson LLP

(57) ABSTRACT

Methods and apparatus for safely forming anastomoses comprise magnetic members configured to accommodate different tissue types and patients of differing size and weight. The magnetic members may comprise first and second magnetic members configured to engage each other with a force sufficient to form anastomosis while taking a sufficiently long time to allow the intestinal walls to fuse together. The first and second magnetic members can be configured to form anastomoses between both similar and different types of intestinal tissue. An elongate surgical placement instrument can be configured to engage and manipulate the first and second magnet members through the intestinal wall from outside the intestinal wall in order to place each of the magnetic members at desired locations.

32 Claims, 12 Drawing Sheets

(52) U.S. Cl.
CPC .............. *A61B 2017/1107* (2013.01); *A61B 2017/1132* (2013.01); *A61B 2017/1135* (2013.01); *A61B 2017/1139* (2013.01)

(58) Field of Classification Search
CPC ..... A61B 2017/1117; A61B 2017/1132; A61B 2017/1135; A61B 2017/1139
See application file for complete search history.

(56) References Cited

U.S. PATENT DOCUMENTS

| | | |
|---|---|---|
| 3,324,521 A | 6/1967 | Humiston |
| 3,372,443 A | 3/1968 | Daddona, Jr. |
| 3,512,519 A | 5/1970 | Hall |
| 3,648,372 A | 3/1972 | Kirschenbaum |
| 3,745,995 A | 7/1973 | Kraus |
| 3,890,953 A | 6/1975 | Kraus et al. |
| 3,915,151 A | 10/1975 | Kraus |
| 3,939,821 A | 2/1976 | Roth |
| 3,986,493 A | 10/1976 | Hendren, III |
| 4,029,091 A | 6/1977 | Von Bezold et al. |
| 4,063,561 A | 12/1977 | Mckenna |
| 4,266,533 A | 5/1981 | Ryaby et al. |
| 4,340,038 A | 7/1982 | Mckean |
| 4,552,134 A | 11/1985 | Binard |
| 4,596,073 A | 6/1986 | Ewald |
| 4,598,712 A | 7/1986 | Rebuffat et al. |
| 4,655,100 A | 4/1987 | Frederick et al. |
| 4,896,668 A | 1/1990 | Popoff et al. |
| 4,931,057 A | 6/1990 | Cummings et al. |
| 4,932,951 A | 6/1990 | Liboff et al. |
| 4,966,602 A | 10/1990 | Rebuffat et al. |
| 5,014,699 A | 5/1991 | Pollack et al. |
| 5,330,486 A | 7/1994 | Wilk |
| 5,458,558 A | 10/1995 | Liboff et al. |
| 5,595,562 A | 1/1997 | Grier |
| 5,595,563 A | 1/1997 | Moisdon |
| 5,626,579 A | 5/1997 | Muschler et al. |
| 5,690,656 A | 11/1997 | Cope et al. |
| 5,704,939 A | 1/1998 | Justin |
| 5,851,188 A | 12/1998 | Bullard et al. |
| 5,984,856 A | 11/1999 | Love et al. |
| 6,006,756 A | 12/1999 | Shadduck |
| 6,022,349 A | 2/2000 | Mcleod et al. |
| 6,024,759 A | 2/2000 | Nuss et al. |
| 6,033,412 A | 3/2000 | Losken et al. |
| 6,063,037 A | 5/2000 | Mittermeier et al. |
| 6,099,542 A | 8/2000 | Cohn et al. |
| 6,113,620 A | 9/2000 | Chung |
| 6,187,041 B1 | 2/2001 | Garonzik |
| 6,190,353 B1 | 2/2001 | Makower et al. |
| 6,200,317 B1 | 3/2001 | Aalsma et al. |
| 6,292,680 B1 | 9/2001 | Somogyi et al. |
| 6,306,075 B1 | 10/2001 | Shadduck |
| 6,352,543 B1 * | 3/2002 | Cole ............... A61B 17/0057 128/898 |
| 6,387,096 B1 | 5/2002 | Hyde, Jr. |
| 6,569,166 B2 | 5/2003 | Gonzalez |
| 6,652,540 B1 | 11/2003 | Cole et al. |
| 6,656,194 B1 | 12/2003 | Gannoe et al. |
| 6,669,709 B1 | 12/2003 | Cohn et al. |
| 6,719,768 B1 | 4/2004 | Cole et al. |
| 6,796,984 B2 | 9/2004 | Soubeiran |
| 6,802,847 B1 | 10/2004 | Carson et al. |
| 6,849,076 B2 | 2/2005 | Blunn et al. |
| 6,998,751 B2 | 2/2006 | Lopatinsky et al. |
| 7,001,402 B2 | 2/2006 | Yencho |
| 7,135,022 B2 | 11/2006 | Kosashvili et al. |
| 7,374,567 B2 | 5/2008 | Heuser |
| 7,481,841 B2 | 1/2009 | Hazebrouck et al. |
| 7,559,951 B2 | 7/2009 | Silvestro et al. |
| 7,753,915 B1 | 7/2010 | Eksler et al. |
| 7,862,502 B2 | 1/2011 | Pope et al. |
| 8,043,290 B2 | 10/2011 | Harrison et al. |
| 8,142,454 B2 | 3/2012 | Harrison et al. |
| 8,439,915 B2 | 5/2013 | Harrison et al. |
| 8,623,036 B2 | 1/2014 | Harrison et al. |
| 8,808,158 B2 | 8/2014 | Harrison et al. |
| 8,915,915 B2 | 12/2014 | Harrison et al. |
| 9,526,652 B2 | 12/2016 | Harrison et al. |
| 9,655,767 B1 | 5/2017 | Harrison et al. |
| 10,500,086 B1 | 12/2019 | Harrison et al. |
| 10,555,787 B2 | 2/2020 | Cook et al. |
| 2002/0072758 A1 | 6/2002 | Reo et al. |
| 2002/0103495 A1 | 8/2002 | Cole |
| 2003/0078610 A1 | 4/2003 | Yedlowski |
| 2003/0144682 A1 | 7/2003 | Qureshi et al. |
| 2004/0030395 A1 | 2/2004 | Blunn et al. |
| 2004/0078038 A1 | 4/2004 | Desinger et al. |
| 2004/0078039 A1 | 4/2004 | Michelson |
| 2004/0116945 A1 | 6/2004 | Sharkawy et al. |
| 2004/0122334 A1 | 6/2004 | Yamashiro |
| 2004/0215214 A1 | 10/2004 | Crews et al. |
| 2005/0021059 A1 | 1/2005 | Cole et al. |
| 2005/0080439 A1 * | 4/2005 | Carson ............... A61B 17/0643 606/153 |
| 2005/0228412 A1 | 10/2005 | Surti |
| 2005/0234555 A1 | 10/2005 | Sutton et al. |
| 2006/0009767 A1 | 1/2006 | Kiester |
| 2006/0036267 A1 | 2/2006 | Saadat et al. |
| 2006/0047282 A1 | 3/2006 | Gordon |
| 2006/0074448 A1 | 4/2006 | Harrison et al. |
| 2006/0079897 A1 | 4/2006 | Harrison et al. |
| 2006/0271107 A1 | 11/2006 | Harrison et al. |
| 2006/0282106 A1 | 12/2006 | Cole et al. |
| 2007/0010834 A1 | 1/2007 | Sharkawy et al. |
| 2007/0072758 A1 | 3/2007 | Van Oosterhout |
| 2007/0118158 A1 | 5/2007 | Deem et al. |
| 2007/0156055 A1 | 7/2007 | Royalty |
| 2007/0173878 A1 | 7/2007 | Heuser |
| 2007/0250162 A1 | 10/2007 | Royalty |
| 2007/0276378 A1 | 11/2007 | Harrison et al. |
| 2008/0108860 A1 | 5/2008 | Bell et al. |
| 2008/0114384 A1 | 5/2008 | Chang et al. |
| 2009/0048618 A1 * | 2/2009 | Harrison ............... A61B 17/70 606/153 |
| 2009/0227828 A1 * | 9/2009 | Swain ............... A61B 17/1114 600/12 |
| 2010/0036399 A1 | 2/2010 | Viola |
| 2011/0144560 A1 * | 6/2011 | Gagner ............... A61B 17/221 604/8 |
| 2011/0160752 A1 * | 6/2011 | Aguirre ............... A61B 17/1114 606/153 |
| 2011/0295285 A1 * | 12/2011 | McWeeney ............ A61B 17/11 606/153 |
| 2012/0184799 A1 | 7/2012 | Harrison et al. |
| 2012/0197062 A1 * | 8/2012 | Requarth ............ A61N 5/1001 600/12 |
| 2013/0253548 A1 * | 9/2013 | Harrison ............... A61B 17/11 606/153 |
| 2014/0128868 A1 | 5/2014 | Harrison et al. |
| 2015/0057687 A1 * | 2/2015 | Gittard .................. A61B 17/11 606/153 |
| 2015/0144142 A1 | 5/2015 | Harrison et al. |
| 2015/0164508 A1 * | 6/2015 | Hernandez ............ A61B 17/11 606/153 |
| 2016/0022266 A1 * | 1/2016 | Lukin .................... A61B 17/11 606/154 |
| 2016/0262761 A1 * | 9/2016 | Beisel ................. A61B 17/1114 |
| 2017/0156658 A1 | 6/2017 | Maharbiz et al. |
| 2019/0053838 A1 | 2/2019 | Cook et al. |
| 2019/0053864 A1 | 2/2019 | Cook et al. |
| 2019/0053908 A1 | 2/2019 | Cook et al. |
| 2019/0083266 A1 | 3/2019 | Cook et al. |

FOREIGN PATENT DOCUMENTS

| | | |
|---|---|---|
| SU | 806005 | 2/1981 |
| WO | WO 01/82803 A1 | 11/2001 |
| WO | WO 2012/099813 A2 | 7/2012 |
| WO | WO 2012/099813 A3 | 10/2012 |

(56) References Cited

FOREIGN PATENT DOCUMENTS

| | | |
|---|---|---|
| WO | WO 2019/056014 A1 | 3/2019 |
| WO | WO 2020/050811 A2 | 3/2020 |

OTHER PUBLICATIONS

PCT International Preliminary Report on Patentability and Written Opinion dated Dec. 31, 2019 issued in PCT/US2018/040129.
U.S. Office Action dated Jun. 27, 2008 issued in U.S. Appl. No. 10/954,995.
U.S. Final Office Action dated Aug. 18, 2009 issued in U.S. Appl. No. 10/954,995.
U.S. Office Action dated Sep. 29, 2009 issued in U.S. Appl. No. 11/222,517.
U.S. Office Action dated Dec. 23, 2008 issued in U.S. Appl. No. 11/431,416.
U.S. Office Action dated Dec. 9, 2009 issued in U.S. Appl. No. 11/677,700.
U.S. Final Office Action dated Jun. 10, 2010 issued in U.S. Appl. No. 11/677,700.
U.S. Office Action dated Apr. 11, 2012 issued in U.S. Appl. No. 11/677,700.
U.S. Final Office Action dated Sep. 25, 2012 issued in U.S. Appl. No. 11/677,700.
U.S. Office Action dated Oct. 26, 2009 issued in U.S. Appl. No. 12/189,330.
U.S. Final Office Action dated May 24, 2010 issued in U.S. Appl. No. 12/189,330.
U.S. Office Action dated Jul. 13, 2011 issued in U.S. Appl. No. 12/189,330.
U.S. Office Action dated Jul. 28, 2014 issued in U.S. Appl. No. 14/155,509.
Obora et al., (1980) "Nonsuture Microvascular Anastomosis using Magnetic Rings", *Neurol Med Chir(Tokyo)* 20: 497-505 (English Abstract with original Japanese Article).
EP Extended Search Report dated Jan. 29, 2021, issued in EP 18824606.0.
Gonzales et al., (2012) "Magnamosis III: delivery of a magnetic compression anastomosis device using minimally invasive endoscopic techniques," *Journal of Pediatric Surgery*, 47: 1291-1295.
Graves et al., (2017) "Magnetic Compression Anastomosis (Magnamosis): First-In-Human Trial," *J Am Coll Surg*, 225(5): 676-681.
Jamshidi et al., (2009) "Magnamosis: magnetic compression anastomosis with comparison to suture and staple techniques," *Journal of Pediatric Surgery*, 44: 222-228.
Pichakron et al., (2011) "Magnamosis II: Magnetic Compression Anastomosis for Minimally Invasive Gastrojejunostomy and Jejunojejunostomy," *J Am Coll Surg*, 212: 42-49.
Wall et al., (2013) "Magnamosis IV: magnetic compression anastomosis for minimally invasive colorectal surgery," *Endoscopy*, 45(8): 643-648.
American College of Surgeons, "A Pair of Medical Magnets Shows Promise as a New Tool for Creating an Anastomosis: Proof-of-concept Study in Patients Shows Use of the Device is Safe, Easy for Surgeons to Use", ScienceDaily, Aug. 23, 2017, 3 pages. www.sciencedaily.com/releases/2017/08/170823140707.htm.
ASGE Technology Assessment Committee, "Magnets in the GI tract" Gastrointestinal Endoscopy, Oct. 2013, vol. 78, No. 4, pp. 561-567, DOI:https://doi.org/10.1016/j.gie.2013.07.020.
CN Office Action dated Sep. 28, 2022, in Application No. CN201880055952.
Ho, Y.H. et al., "Techniques for Colorectal Anastomosis", World Journal Gastroenterology, Apr. 7, 2010, vol. 16, No. 13, pp. 1610-1621.
Summary of Clinical Testing—U.S. Appl. No. 16/625,050, covering clinical trials conducted in 2014-2016.
CN Office Action dated Sep. 28, 2022, in Application No. CN201880055952.X with English translation.

* cited by examiner

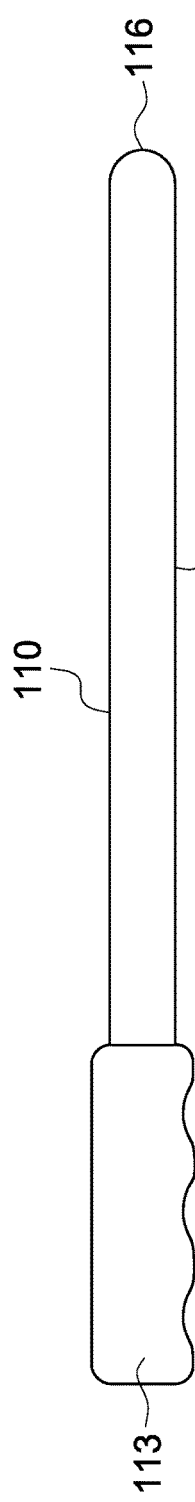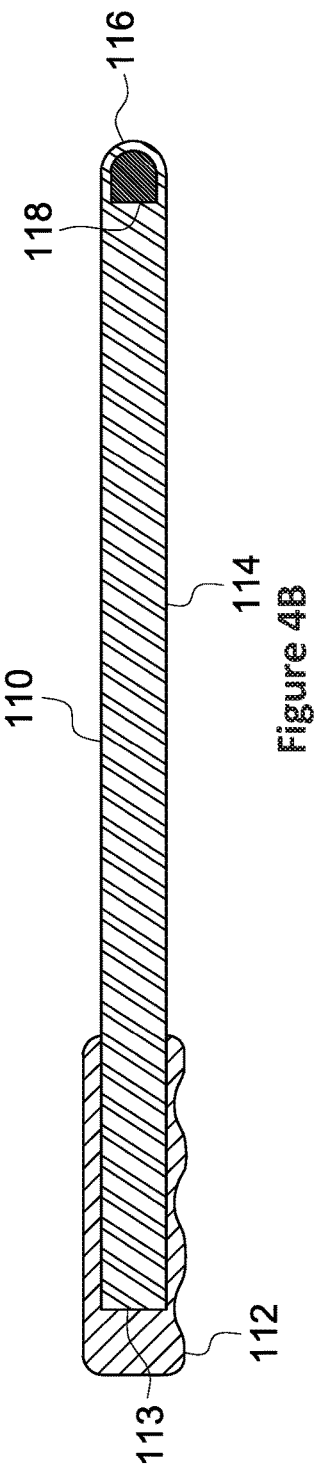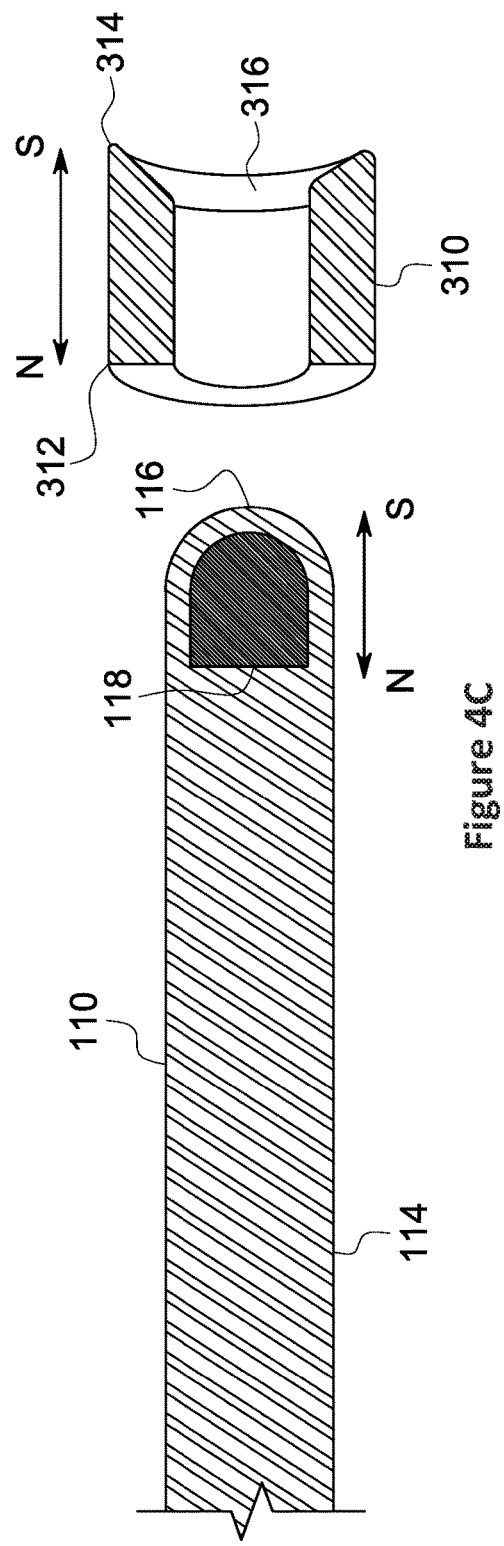

MAGNETIC DEVICES, SYSTEMS, AND METHODS

CROSS-REFERENCE TO RELATED APPLICATIONS

This application is a U.S. 371 National Phase of PCT/US2018/040129, filed on Jun. 28, 2018, which claims benefit of priority under 35 U.S.C. § 119(e) to U.S. Provisional Patent Application No. 62/527,690, filed Jun. 30, 2017, both of which are hereby incorporated herein by reference in their entirety and for all purposes.

STATEMENT OF GOVERNMENT SPONSORED SUPPORT

This invention was made with Government support under contract P50 FD003793 awarded by the FDA Pediatric Device Consortium. The Government has certain rights in the invention.

FIELD OF THE INVENTION

This invention relates to magnetic devices, systems and methods for forming anastomoses.

BACKGROUND OF THE INVENTION

Anastomosis in biological systems can refer to the formation of connections between two biological tissues or structures. Biological anastomosis can occur between tubular biological structures, such as between blood vessels or between loops of the intestine. Intestinal anastomosis can be achieved surgically through resection of a segment of the intestine and joining of the two remaining ends of the intestine, which can then be sewed or stapled together. When forming an anastomosis between sections of gastrointestinal tissue, leakage of the anastomosis can potentially cause undesirable consequences to the patient, and the prior approaches may not be well suited for use with large numbers of patients. Also, at least some of the prior approaches can be somewhat more invasive than would be ideal.

Although magnets have been proposed to form anastomoses, the prior methods and apparatus can be less than ideal in at least some instances. For example, prior magnets used to form anastomoses can be less versatile than would be idea. Some of the prior approaches may not be well suited for use with patients of different size and ages. Also, some of the prior approaches, while capable of forming an anastomosis for tissue one type of tissue may not be well suited for anastomosing tissue of different types. The force of attraction between a magnetic pair generally decreases with distances, and the prior approaches can be more sensitive to differences in tissue thickness than would be ideal. Further, at least some of the prior magnetic approaches for forming anastomoses may not be well suited for use with readily available surgical instruments, and may be more complex than would be ideal.

Prior methods and apparatus to deliver magnets to target sites can be less than ideal, and the size of the incision and surgical access to the anastomosis site has been less than ideally addressed by prior approaches in at least some instances. Also, the placement of the magnetic members at a desired target location can be less than ideal with at least some of the prior approaches.

SUMMARY OF THE INVENTION

The methods and apparatus for safely forming anastomoses may include magnetic members configured to accommodate different tissue types and patients of differing size and weight. The magnetic members may include first and second magnetic members configured to engage each other with a force sufficient to form anastomosis while taking a sufficiently long time to allow the intestinal walls to fuse together, such as with scar tissue. The first and second magnetic members may include engagement surfaces configured to provide a tissue pressure gradient profile which allows the use of increased force and formation of the anastomosis over a sufficient time. The first and second magnetic members may include a pair of magnetic members. The first and second magnetic members can be configured to form anastomoses between both similar and different types of intestinal tissue, such as between small intestinal duodenum tissue and small intestinal tissue past the duodenum, small intestinal tissue past the duodenum and small intestinal tissue past the duodenum, and between small intestinal and gastric tissue. The first and second magnetic members may be configured with a size, shape and magnetic force between the magnetic members to form the anastomosis between similar and different tissue types of tissue with a sufficient force to allow healing, such as at least 6 Newton (N), and this amount of force can be sufficient to accommodate variability among different patients and tissue thicknesses. The first and second magnetic members include tissue engagement surfaces configured to engage the tissue and form the anastomosis over a sufficiently long time with increased amounts of force. The tissue engagement surface of the first and second magnetic members can be inclined in relation to each other in order to provide the pressure gradient to the tissue. Each of the first and second magnetic members can be configured to be slid along the intestinal wall with a surgical instrument located outside the intestine without substantially damaging tissue. The magnetic members may include edges shaped to form an anastomosis with decreased sharpness in order to allow the magnetic members to slide along the intestinal wall.

An elongate surgical placement instrument external to a lumen can be configured to engage and manipulate a magnetic member placed within the lumen with magnetic engagement through the luminal wall in order to place the magnetic member at desired locations within the lumen. This approach can decrease the invasiveness of the procedure and allow use with many types of magnets and magnetic materials in order to form anastomoses. This approach can be well suited for placement of magnetic member in the lumen of the small intestine, without penetrating the wall of the small intestine. The elongate placement instrument may include a magnetic material configured with the magnetic member to provide sufficient force near a distal end of the instrument in order to engage the magnetic member through the luminal wall such as an intestinal wall, and to manipulate the magnetic member within the lumen. The amount of force can be within a range so as to allow the surgical instrument to manipulate the magnetic member within the lumen from outside the lumen and to allow the surgical instrument to be disengaged from the magnetic member when placed at a desired location inside the intestinal lumen. The amount of force may include no more than about 6 N, and a distal end portion of the placement instrument can be rounded and shaped to decrease pressure to the luminal wall when the distal end portion engages the magnetic member. The placement instrument and the magnetic member may include smooth surfaces to facilitate sliding of the magnetic member and distal portion of the placement instrument. A plurality of surgical placement instruments, in which each instrument includes a magnetic material can be used to place the magnetic members.

Anastomosis in biological systems can refer to the formation of connections between two biological tissues or structures. Biological anastomosis can occur between tubular biological structures, such as between blood vessels or between loops of the intestine. Intestinal anastomosis can be achieved surgically through resection of a segment of the intestine and joining of the two remaining ends of the intestine, which can then be sewed or stapled together. When forming an anastomosis between sections of gastrointestinal tissue, leakage of the anastomosis can potentially cause undesirable consequences to the patient, and the prior approaches may not be well suited for use with large numbers of patients. Also, at least some of the prior approaches can be somewhat more invasive than would be ideal.

Although magnets have been proposed to form anastomoses, the prior methods and apparatus can be less than ideal in at least some instances. For example, prior magnets used to form anastomoses can be less versatile than would be ideal. Some of the prior approaches may not be well suited for use with patients of different size and ages. Also, some of the prior approaches, while capable of forming an anastomosis for tissue one type of tissue may not be well suited for anastomosing tissue of different types. The force of attraction between a magnetic member pair generally decreases with distances, and the prior approaches can be more sensitive to differences in tissue thickness than would be ideal. Further, at least some of the prior magnetic approaches for forming anastomoses may not be well suited for use with readily available surgical instruments, and may be more complex than would be ideal.

Prior methods and apparatus to deliver magnets to target sites can be less than ideal, and the size of the incision and surgical access to the anastomosis site has been less than ideally addressed by prior approaches in at least some instances. Also, the placement of the magnetic members at a desired target location can be less than ideal with at least some of the prior approaches.

In some implementations, a system is provided for forming an anastomosis between two lumens or two locations in a lumen of a patient. The system may include a first magnetic member configured to be located adjacent a first luminal tissue region at a first location and a second magnetic member configured to be located adjacent a second luminal tissue region at a second location. The first magnetic member may have a first engagement surface that faces a second engagement surface of the second magnetic member when the first magnetic member and the second magnetic member are magnetically coupled to one another with the first and second luminal tissue regions interposed therebetween, the first engagement surface may have a first average radial cross-sectional profile, the second engagement surface may have a second average radial cross-sectional profile, and a linear distance between the first average radial cross-sectional profile and the second average radial cross-sectional profile may increase with increasing radial distance from an innermost portion of the first and second magnetic members, and the first engagement surface and the second engagement surface may be configured, when the first magnetic member and the second magnetic member are magnetically coupled together with the first and second luminal tissue regions interposed therebetween, to exert a pressure of between 20 kPa and 80 kPa on nominally annular first portions of the first and second luminal tissue regions located along interior edges of the first and second magnetic members and a pressure of 0 kPa to 15 kPa along nominally annular second portions of the first and second luminal tissue regions located along exterior edges of the first and second magnetic members.

In some implementations, the first engagement surface and the second engagement surface may be inclined relative to one another when the second magnetic member is magnetically aligned with the first magnetic member.

In some implementations, the first engagement surface and the second engagement surface may each have radial profiles dimensioned to provide a gap between portions of the first engagement surface and the second engagement surface, and the gap may be within a range from about 0.65 mm to about 0.85 mm when other portions of the first engagement surface and the second engagement surface located radially inward of the gap are brought into contact with one another.

In some implementations, when the first magnetic member and the second magnetic member are brought into contact with one another such that the first engagement surface contacts the second engagement surface at inner locations near inner boundaries of the first and second engagement surfaces, the gap may exist between the first and second engagement surfaces near outer boundaries of the first and second engagement surfaces. In some such implementations, the first location may be within about 0.25 mm of the inner boundaries and the second location may be within about 0.25 mm of the outer boundaries.

In some implementations, the first engagement surface and the second engagement surface may be configured, when the first magnetic member and the second magnetic member are magnetically coupled together with 4 mm to 8 mm of combined uncompressed thickness of the first and second luminal tissue regions initially interposed therebetween, to exert the pressure of between 20 kPa and 80 kPa on the nominally annular first portions and a pressure of 0 kPa to 15 kPa along the nominally annular second portions.

In some implementations of the system, the pressure exerted on the nominally annular first portions may be greater than the pressure exerted on the nominally annular second portions by at least a factor of 5.

In some implementations of the system, the first and second magnetic members may be configured such that within an hour of the first and second magnetic members having been magnetically coupled to each other with the first and second luminal tissue regions compressed therebetween, the pressure exerted on the nominally annular first portions may be within a range from about 25 kPa to about 53 kPa and the pressure exerted on the nominally annular second portions may be within a range from about 2 kPa to about 12 kPa.

In some implementations of the system, the first average radial cross-sectional profile may extend across a radial length of no more than about 8 mm.

In some implementations of the system, the first average radial cross-sectional profile may extend across a radial length of no more than about 2 mm.

In some implementations of the system, the system may further include an instrument for guiding the first magnetic member within the lumen or one of the lumens. The instrument may include an elongate member having a distal portion and a proximal portion. The instrument may also include a magnetic material located on the distal portion of the elongate member. The magnetic material may be configured to magnetically couple with the first magnetic member with the first luminal tissue region interposed therebetween and with a force of no more than about 6N to allow the first magnetic member to be guided towards a target location for forming the anastomosis using the instrument.

In some implementations, the distal end of the instrument may have a shape that is complementary to a shape of the first magnetic member with which the instrument is configured to magnetically couple.

In some implementations, the magnetic material in the instrument may be configured to magnetically couple to the first magnetic member with the first luminal tissue region interposed therebetween with an attractive force that is less than an attractive force that would exist between the first magnetic member and the second magnetic member when the first magnetic member and the second magnetic member are magnetically coupled together with the first and second luminal tissue regions interposed therebetween.

In some implementations, a method of placing a first magnetic member using the system discussed above may be provided. The method may include magnetically coupling the first magnetic member with the distal portion of the instrument and guiding the first magnetic member to the first luminal tissue region with the distal portion of the instrument.

In some further implementations of the method, the method may further include decoupling the first magnetic member from the distal portion when the second magnetic member has been placed at the second luminal tissue region and the first magnetic member and the second magnetic member have magnetically coupled with one another with the first and second luminal tissue regions interposed therebetween.

In some implementations of the system or method, the first magnetic member, the second magnetic member, or the first and second magnetic members may each have a maximum dimension equal to or less than about 25 mm.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative implementations, in which the principles of the invention are utilized, and the accompanying drawings of which:

FIG. 4A shows a schematic diagram of a placement instrument, in accordance with some implementations.

FIG. 4B shows a schematic diagram of a placement instrument as in FIG. 4A in cross-section.

FIG. 4C shows an enlarged view of view of a placement instrument as in FIGS. 4A and 4B with a magnetic member in cross-section, in accordance with some implementations.

DETAILED DESCRIPTION

Figure 1:
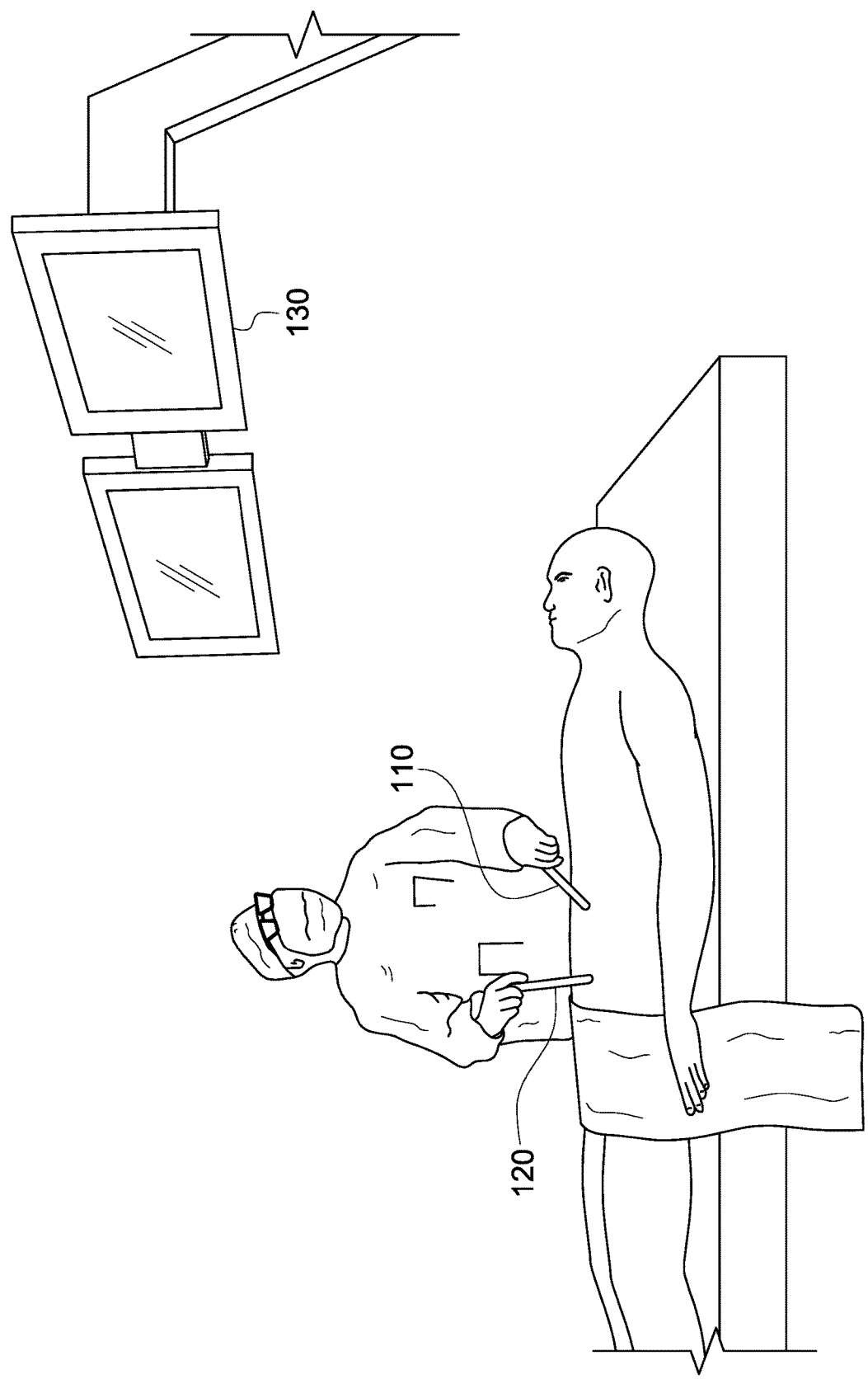
FIG. 1 shows manipulation of magnetic members in accordance with some implementations.

The methods and apparatus disclosed herein are well suited for forming anastomoses between tissue structures, such as side-to-side anastomoses of gastro-intestinal tissue structures, end-to-side anastomoses, and end-to-end anastomoses. The presently disclosed methods and apparatus are well suited for combination with many prior approaches to forming anastomoses, and can be combined with laparoscopes, laparoscopic instruments, and insufflation so as to require minimally invasive access to a patient. The presently disclosed methods and apparatus are well suited to access the gastrointestinal tract of a patient with the natural orifices of the patient in combination with known instruments such as endoscopes and colonoscopes, for example. A magnetic member as disclosed herein can be delivered orally and advanced to the stomach with an endoscope, for example, and placed at a location along or in the jejunum with a magnetic placement instrument, for example. A wire snare can be used with the endoscope to advance the magnetic member along the stomach to the duodenum and release it, for example. Alternatively or in combination, a magnetic member can be inserted into the patient and advanced with a colonoscope to the ileocecal valve, and advanced to a target location of the jejunum with a magnetic placement instrument, for example. In some instances, a small laparoscopic incision in the skin of the patient can be used to access the exterior of the jejunum with a magnetic placement instrument and to engage the magnetic member though the wall of the jejunum without penetrating the wall of jejunum, for example. The first and second magnetic members can then be brought into engagement with each other to form an anastomosis at desired locations of the tissues to be joined by the anastomosis.

As used herein, "and/or" encompasses alternative stated possibilities and combinations thereof. For example A and/or B encompasses either A or B and combinations of A and B. Similarly, A, B, and/or C encompasses A, B, C, AB, AC, BC, or ABC, and so forth.

As used herein, terms such as colon, small intestine, stomach, duodenum, ileum, side-to-side anastomoses, side-to-end anastomosis, end-to-end anastomosis, jejunum and jejunojejunostomy are used in accordance with their clinically accepted meanings. For example, jejunojejunostomy refers to an opening (anastomosis) created between two parts of the jejunum, and the jejunum refers the part of the small intestine between the duodenum and ileum.

In some situations, it can be advantageous to join together two or more organs or biological tissues. For example, in some situations, which can include bowel obstructions, trauma to a region of the gastrointestinal tract, or disease of a region of the gastrointestinal tract, it can be advantageous to shorten or to bypass one or more sections of the gastrointestinal tract by joining together regions of the gastrointestinal tract on either side of the affected section. The presently disclosed methods and apparatus are well-suited for forming anastomoses for treating diabetes, such as side-to-side anastomoses of the gastro-intestinal tract, for example side-to-side anastomoses of the duodenum and the jejunum.

Two or more biological tissues or organs can be joined together through the application of a compressive force, as may be provided, for example, by magnets. In some cases, the compressive force can be at least about 6 newtons (6 N). In some cases, at least one of the two or more biological tissues or organs being joined with a compressive force can include an interior space (e.g., a lumen of a biological tissue or organ). In some cases, such a joining of two or more biological tissues with compressive force can create a channel (e.g., an anastomosis) between the interior spaces (e.g., the lumens) of the two or more biological tissues. For example, an anastomosis can be created between a first and second region of the gastrointestinal tract (e.g., a channel putting a first region of the gastrointestinal tract in fluidic communication with a second region of the gastrointestinal tract) using compressive force, such as a magnetic force. The first and second regions of the gastrointestinal tract can be joined and a channel created between the lumen of the first region of the gastrointestinal tract and the lumen of the second region of the gastrointestinal tract. In some cases, the use of compressive force to create an anastomosis in this way can place the lumen of the first region of the gastrointestinal tract and second region of the gastrointestinal tract into direct fluidic communication with one another through the channel created by the anastomosis.

The compressive force between the two or more biological tissues to be joined with an anastomosis can be created through a magnetic attraction between a first magnetic member and a second magnetic member, each of which includes a magnetic material. A magnetic material, as the term is used herein, refers to a material that either generates a magnetic field, e.g., a magnet or other magnetized material, or that is capable of being magnetized, e.g., ferritic materials; in this application, in a matched pair of magnetic members or a magnetic member and placement instrument, at least one of the two components will include a magnet or magnetized material, while the other may similarly have a magnet or magnetized material or may simply have a magnetizable material. For example, a first magnetic member can be located in the lumen of a first region of a biological tissue (e.g., the lumen of a first region of the gastrointestinal tract) and a second magnetic member can be located in the lumen of a second region of a biological tissue (e.g., the lumen of a second region of the gastrointestinal tract).

A magnetic member can be placed or positioned in a region of the patient in many ways. For example, an elongate magnetic placement instrument can be used to aid in the placement or positioning of the magnetic member either with respect to a target region of the body or with respect to the position or orientation of another magnetic member. The elongate instrument can be used to place or to position the magnetic member at a desired target location in the body. In some cases, the instrument includes a handle, an elongate shaft and a magnetic material located near a distal end. For example, the elongate member can include a handle at its proximal end and a magnetic material at its distal end. The distal end can be used to engage a magnetic member through magnetic attraction in order to aid in the placement and positioning of the magnetic member. In some cases, the elongate member engages the magnetic member through a wall of a biological tissue, for example, without penetrating the wall of the biological tissue. For example, the elongate member outside of a tissue or organ can interact with a magnetic member located in the lumen of the tissue or organ with magnetic attractive forces through a wall. In some cases, the force between the elongate member and the magnetic member during placement and positioning includes no more than about 6 N. In some cases, the magnetic material of the elongate member and the magnetic member can be configured to engage one another through the luminal wall with a pressure within a range from about 5 kPa to about 10 kPa, from about 10 kPa to about 15 kPa, from about 10 kPa to about 20 kPa, from about 20 kPa to about 30 kPa, from about 30 kPa to about 40 kPa, from about 40 kPa to about 50 kPa, no more than about 50 kPa, no more than about 40 kPa, no more than about 30 kPa, no more than about 20 kPa, or no more than about 10 kPa. In some cases, the elongate member can slide along an exterior surface of the wall of the lumen thereby causing the magnetic member to form the anastomosis to slide along an interior surface of the wall of the lumen in order to place the magnetic member at a desired target location to form the anastomosis. The magnetic member may include rounded edges in order to decrease friction and pressure to the tissue along which the magnetic member is moved when engaged with the placement instrument. A magnetic member can be placed or positioned using an elongate member so that it is placed or positioned at a target region of the body (e.g., the target region of a lumen of the gastrointestinal tract). A first magnetic member can be placed or positioned in a first target region of the body using an elongate member so that it is in close proximity with and engages the second magnetic member located in a second target region of the body.

When placed in close proximity with one another, the first and second magnetic members, which may be referred to collectively as a magnetic member pair, magnetically associate and engage with one another with the luminal wall(s) disposed in between. In some cases, the magnetic attraction between the first and second magnetic members can be at least about 6 Newtons (6 N), although lower amounts of force may be used. The force of compression caused by the association of the first and second magnetic members with one another and experienced by the biological tissue disposed between them can cause remodeling of the biological tissue such that an anastomosis is formed between the regions of the body in which the first and second magnetic members are located (e.g., the first and second region of the gastrointestinal tract). In some cases, the force of compression can cause necrosis of the tissue disposed between and/or compressed by the first and second magnetic members, and scar tissue can form in proximity to the necrotized tissue so as to bond the first luminal wall to the second luminal wall at the first and second placement locations.

The anastomosis caused by the compression of the biological tissue by the first and second magnetic members can result in the first and second region of biological tissue sharing direct fluidic communication at the location of the anastomosis. The method of creating an anastomosis can, therefore, be used to create an alternate channel for fluidic communication in a patient requiring such an intervention. For example, an anastomosis can be created in a patient by compressing a first and second region of the gastrointestinal tract using first and second magnetic members located, respectively, in the first and second regions of the gastrointestinal tract to form a gastrointestinal bypass.

Clinical Use of a Magnetic Member Pair to Form an Anastomosis

Reference is now made to FIG. 1, which illustrates non-limiting representations of the use of at least one placement instrument 110 to manipulate one or more magnetic members in a clinical setting. For example, a healthcare provider such as a physician may utilize the placement instrument 110 during bypass surgeries, such as bariatric, Roux-en-Y gastric bypass, mini-gastric bypass, or endoscopic duodenal-jejunal bypass surgeries. In some cases, one or more magnetic members can be used to treat a patient. As an example, one or more magnetic members may be used to treat a patient with diabetes. In some cases, a magnetic member pair can be used to create an intestinal anastomosis in a patient with diabetes rather than a stapled or hand-sewn anastomosis in order to reduce the likelihood of anastomosis leakage. The treating of a patient can include placement (e.g., installation) (and optionally retrieval) of one or more magnetic members into one or more regions of the patient's body. The regions can include a target region of the patient's body. In some instances, the target regions may include a cavity within the patient's body, or tubular structures within the patient's body such as one or more blood vessels, one or more portions of the central nervous system (e.g., the ventricles of the brain), one or more portions of the biliary tract, or one or more portions of the alimentary canal.

Regions of the biliary tract can be joined through anastomosis using compression with a magnetic member pair. For example, an end-to-end ductal anastomosis can be created with a magnetic member pair in liver transplant patients or in the treatment of iatrogenic bile duct injuries.

Installation of a magnetic member can include insertion and/or positioning of the magnetic member. In some instances, installation of two or more magnetic members (e.g. a magnetic member pair) can be performed to create an anastomosis at a target region (e.g., a target location). A target region can include one or more luminal walls, for example. In some instances, a target region can include a first luminal wall and a second luminal wall. Optionally, the target region may include a first location of a luminal wall of a first lumen of the patient's body and a second location of the same luminal wall of the first lumen of the patient's body.

The lumen can include any space in the body enclosed by biological tissue. For example, the lumen can include the interior space of a tubular structure or non-tubular structure of the body, such as any region of the gastrointestinal tract, a region of the biliary tract (e.g., gall bladder, hepatic duct, cystic duct, bile ducts, or vessels of the liver), a region of the central nervous system (e.g., the ventricles of the brain), a region of the vascular system (e.g., blood vessels), a region of a lymphatic system, a region of the respiratory tract, a region of the renal system, a region of the urinary tract, or a region of the reproductive tract (e.g., the fallopian tubes, uterus, vagina, vas deferens, and the like). The lumen can include a space that contains a liquid, a solid, a gas, a semi-solid material, or any combination thereof.

The target region can include one or more luminal walls from one or more organs or regions of the body. For example, a target region can include a luminal wall of the stomach and a luminal wall of the small intestine, and the target region can be the intended site of an anastomosis to be formed using a magnetic member pair. A first target region can be within about 7 feet, within about 6 feet, within about 5 feet, within about 4 feet, within about 3 feet, within about 2 feet, within about 1 foot, or within about 6 inches of a patient's duodenum (e.g., as measured in distance along the gastrointestinal tract), or within a range defined by any two of the preceding values. A second target region can be within about 7 feet, within about 6 feet, within about 5 feet, within about 4 feet, within about 3 feet, within about 2 feet, within about 1 foot, or within about 6 inches of a patient's ileocecal valve, or within a range defined by any two of the preceding values. The first target location and the second target location can each be located in the patient's jejunum and placed at a location within the preceding ranges. For example, a side-to-side anastomosis can be formed using a first and second magnetic member such that the anastomosis joins a target area located within about 6 feet of a patient's duodenum with a second target area located within about 6 feet of a patient's ileocecal valve, in order to treat diabetes.

Installation or introduction of a magnetic member can be accomplished surgically, transdermally, orally, or rectally, for example, although in many cases a magnetic member is introduced orally and another magnetic member is introduced rectally to form a side-to-side anastomosis.

An elongate placement instrument 110 can be introduced into a patient through the skin and/or muscle layers in order to manipulate the magnetic member. For example, the placement instrument may be introduced into a patient through the skin and muscle layers of the abdominal region of the patient into the abdominal cavity. The placement instrument may be introduced into the patient to place, position, or reposition one or more magnetic members in the patient's body. In some instances, the placement instrument is introduced into the tissue of the patient's body directly. Optionally, the placement instrument can also be introduced into the tissue of the patient's body indirectly, e.g. with the aid of a secondary device, such as a cannula, a sheath, the channel of an endoscope, a surgical robot, and the like.

In some cases, one or more additional tools or instruments 120 can be used with the one or more placement instruments 110 to install, manipulate, place, position, and/or remove the one or more magnetic members, which can be located inside of body (e.g., inside of the abdominal cavity). The additional tool or instrument 120 can include a laparoscope, an endoscope, a snare, surgical forceps, a surgical stapler, a cystoscope, an endocutter, a cannula, a guidewire, a catheter, a sheath (e.g., an endoscopy sheath), a suturing device (e.g., a needle holder), a clip applier, a grasper, a scalpel, a probing instrument (e.g., a probe), a retractor, a hook, a hose (e.g., an insufflator for delivering gases such as carbon dioxide ($CO_2$) into the patient's body), a light projection device, a microscope, a sensor (e.g., a thermometer, a pH meter, a pressure sensor, or the like), an optical sensor (e.g., a video camera or a detector such as a fluorescence detector), or any similar device. Each of the aforementioned surgical instruments, such as the forceps may include non-magnetic materials in order to decrease magnetic attraction and related interference with the magnetic member. In at least some instances, the additional tool or instrument may consist of non-magnetic materials in order to inhibit interaction with the magnetic member.

The additional tool or instrument 120 can be used to manipulate tissues or devices described herein. In some instances, additional tools or instruments can be utilized in the processes described herein. For example, additional tools may be provided to illuminate or image surgical surfaces and tissues during surgical procedures (e.g., involving installation, manipulation, or retrieval of magnetic members). The additional tools or instruments can be rigid or flexible. An additional tool or instrument 120 can be operated manually or robotically with known surgical robots and combinations thereof. The additional tool or instrument 120 can also include a magnetic material (such as iron, a magnetic rare-earth element, or an electromagnet). Alternatively, the additional tool or instrument may include a non-magnetic material.

Images recorded or transmitted from the one or more additional tools or instruments 120 can be displayed on a monitor or screen 130 during surgical procedures to aid in, for example, the installation, manipulation, positioning, or retrieval of magnetic members. The one or more additional tools or instruments 120 can communicate with the monitor wirelessly or through direct electrical connections, each of which can be routed to or through a computer, a server, or a communication hub.

Anastomoses of the Alimentary Canal

Figure 2:
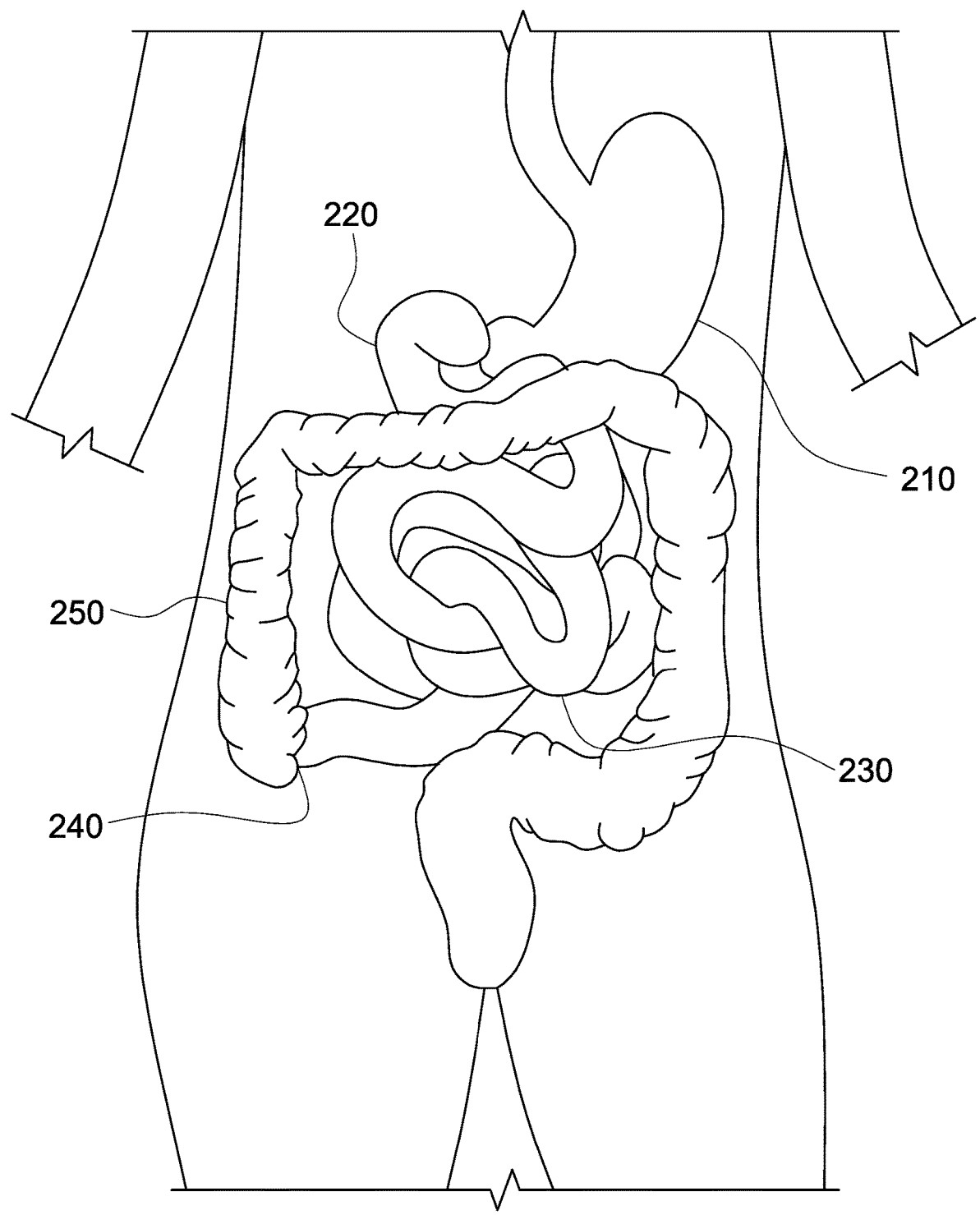
FIG. 2 shows partial anatomy of the abdomen, in accordance with some implementations.

FIG. 2 shows a partial anatomy of the alimentary canal in the abdominal cavity. The alimentary canal includes several regions that can be joined through anastomosis, including the stomach 210, the duodenum 220, the small intestine 230, the ileocecal valve 240, and the colon 250. These and other regions of the alimentary canal can be affected with adverse biological conditions such as full or partial blockages and obstructions, tumors and cancers, perforations and other traumatic injury, inflammation, infections (e.g., viral infections, parasitic infections, and the like), or intussusception. In some cases, the adverse biological conditions may be treated surgically (e.g., with a procedure including the formation of an anastomosis).

A target region for anastomosis can include any region of the gastrointestinal tract (e.g., the alimentary canal). For example, a target region can include a region of the stomach, duodenum, small intestines, ileocecal valve, or colon. A small intestine target location can include a location of the duodenum, jejunum, or ileum. For example, a side-to-side anastomosis can be formed joining a first region of the small intestine to a second region of the small intestine or small intestine 230 to stomach 210 in as few as 14 days, 13 days, 12 days, 11 days, 10 days, 9 days, 8 days, 7 days, 6 days, 5 days, 4 days, 3 days, or within a range defined by any two of the preceding values. In another example, an end-to-side anastomoses can be formed joining a closed end region of a small intestine 230 (e.g., after the intestine has been cut to create an end region and closed surgically) to a region of a stomach 210 wall in as few as 14 days, 13 days, 12 days, 11 days, 10 days, 9 days, 8 days, 7 days, 6 days, 5 days, 4 days, 3 days, or a range defined by any two of the preceding values. In another example, end-to-end anastomosis can be formed joining a first closed end region of a small intestine with a second closed end region of the small intestine in as few as 14 days, 13 days, 12 days, 11 days, 10 days, 9 days, 8 days, 7 days, 6 days, 5 days, 4 days, 3 days, or a range defined by any two of the preceding values.

An anastomosis of the alimentary canal can be formed by positioning a first magnetic member and a second magnetic member of a magnetic member pair (e.g., an upper magnetic member and a lower magnetic member) in separate regions of the alimentary canal (e.g., a first target region and a second target region). The first magnetic member and the second magnetic member may be brought into close enough proximity with one another so as to engage one another (e.g., through magnetic attraction). When biological tissue is disposed between the first and second magnetic member while the first and second magnetic members are engaged with one another, the tissue is typically compressed. Compression of tissue between the members of a magnetic member pair can cause the intervening tissue (e.g., the tissue disposed between the magnetic members) to be compressed so as to join and form an anastomosis. In some instances, the size of the magnetic members, the relative shape of the magnetic members, and/or the attractive force between the magnetic members may affect whether and how the anastomosis is formed. In some instances, the formation of an anastomosis using magnetic members can cause separate regions of the alimentary canal to be in fluidic communication. For example, a side-to-side intestinal anastomosis can include joining the wall of a first region of the small intestine (e.g., a first small intestine location) with the wall of a second region of the small intestine (e.g., a second small intestine location) such that the intestinal lumen of the first region is in fluidic communication with the intestinal lumen of the second region. In certain instances, an end-to-end anastomosis formed using magnetic members can include joining the ileocecal valve 240 to a closed-end region of the duodenum 220. An end-to-end anastomosis joining the ileocecal valve and a closed-end region of the duodenum in such a fashion can place the ileocecal valve in direct fluidic communication with the duodenum. In some cases, an end-to-side anastomosis formed using magnetic members can include joining a region of the small intestine 230 (e.g., a small intestine location such as a region of the jejunum or a region of the ileum) to a wall of the stomach 210 (e.g., a stomach location). An end-to-side anastomosis joining the small intestine and stomach in such a fashion can place the stomach and jejunal or ileal small intestine in direct fluidic communication (e.g., such that fluid can be communicated from the stomach to the small intestine without passing through the duodenum).

The combined thickness of a first and second biological tissue (e.g., a first and second luminal tissue region) can be within a range from about 4 mm to about 8 mm prior to compression and within a range from about 2 mm to 4 mm upon placement of the first and second magnetic members, e.g., within a few minutes or about one hour of placement. For example, small intestinal tissue may include a thickness within a range from about 2 to 3 mm, and the stomach tissue may include a thickness within a range from about 4 to 5 mm of thickness. Upon compression with the magnetic member pair the thickness of the tissue decreases to about half of the uncompressed thickness. As the tissue necrotized, the thickness of the compressed necrotizes tissue decreases further.

Magnetic Members and Magnetic Member Pairs

FIGS. 3A-3G show implementations of magnetic members and magnetic member pairs. A magnetic member pair 330 can include a first magnetic member 310 (e.g., an upper magnetic member) and a second magnetic member 320 (e.g., a lower magnetic member). The first magnetic member 310 can include a first engagement edge 314 and the second member 320 may include a second engagement edge 324. The first magnetic member 310 may include a first inner portion including a first engagement surface 316, and the second magnetic member 320 may include a second inner portion including a second engagement surface 326. In some instances, a magnetic member can also include an outer edge or corner (e.g., a first outer edge 312 and/or a second outer edge 322—see FIG. 3G). Each of the first magnetic member 310 and the second magnetic member 320 can include an outer surface, and, in some instances, the outer surface can be defined by a covering such as a casing, a housing or a coating for enclosing the magnetic material or magnetic core of the magnetic member. The covering can include a variety of biocompatible materials commonly used with implantable devices, including plastic, polytetrafluoroethylene (PTFE), polycarbonate, a metal or metallic alloy, a biocompatible non-ferromagnetic material, silicone, and/or many other biocompatible materials known to one of ordinary skill in the art. In some instances, a magnetic member can include a force sensor, which can be used to measure force (e.g., the compressive force between a first magnetic member and a second magnetic member of a magnetic member pair).

The overall geometry or the inner opening of the magnetic member can include various shapes, including circular, oval, or polygonal, and may also be annular. In some instances, the annular magnetic member includes an inner edge defined by an inner diameter and an outer edge defined by an outer diameter. The inner edge can be circular, oval, or polygonal in shape and can define an opening (e.g., as in an annular magnetic member). In some cases, a first or second magnetic member includes a flat surface (e.g., an outer surface of a magnetic member), a convex surface (e.g., an engagement surface of a second magnetic member), or a concave surface (e.g., an engagement surface of a first magnetic member). For example, a first magnetic member can include a concave surface complementary to a convex surface on a second magnetic member. In some cases, an engagement surface of a first magnetic member (e.g., first engagement surface 316) can include a substantially flat surface, and an engagement surface of the second magnetic member (e.g., second engagement surface 326) includes an inclined surface relative to the engagement surface of the first magnetic member.

Although each of the first magnetic member 310 and the second magnetic member 320 may include pre-assembled pieces, each of the first and second members may include segments configured for in situ assembly within the patient. Each magnetic member can include segments, and, the magnetic member segments can be separable from one another prior to insertion, or configured to extend in a substantially elongate configuration for passage along an endoscope tube, and combinations thereof. Each of the magnetic member segments may include magnetic materials capable of producing a magnetic field, in order to provide attractive forces between the first and second members, or for self-assembly. The magnetic member segments can be configured for self-assembly (e.g., through alignment of magnetic fields and a resulting mutual magnetic attraction). Alternatively or in combination, the segments can be configured for in situ assembly with other structures such as wires and hinges, for example.

Figure 10:
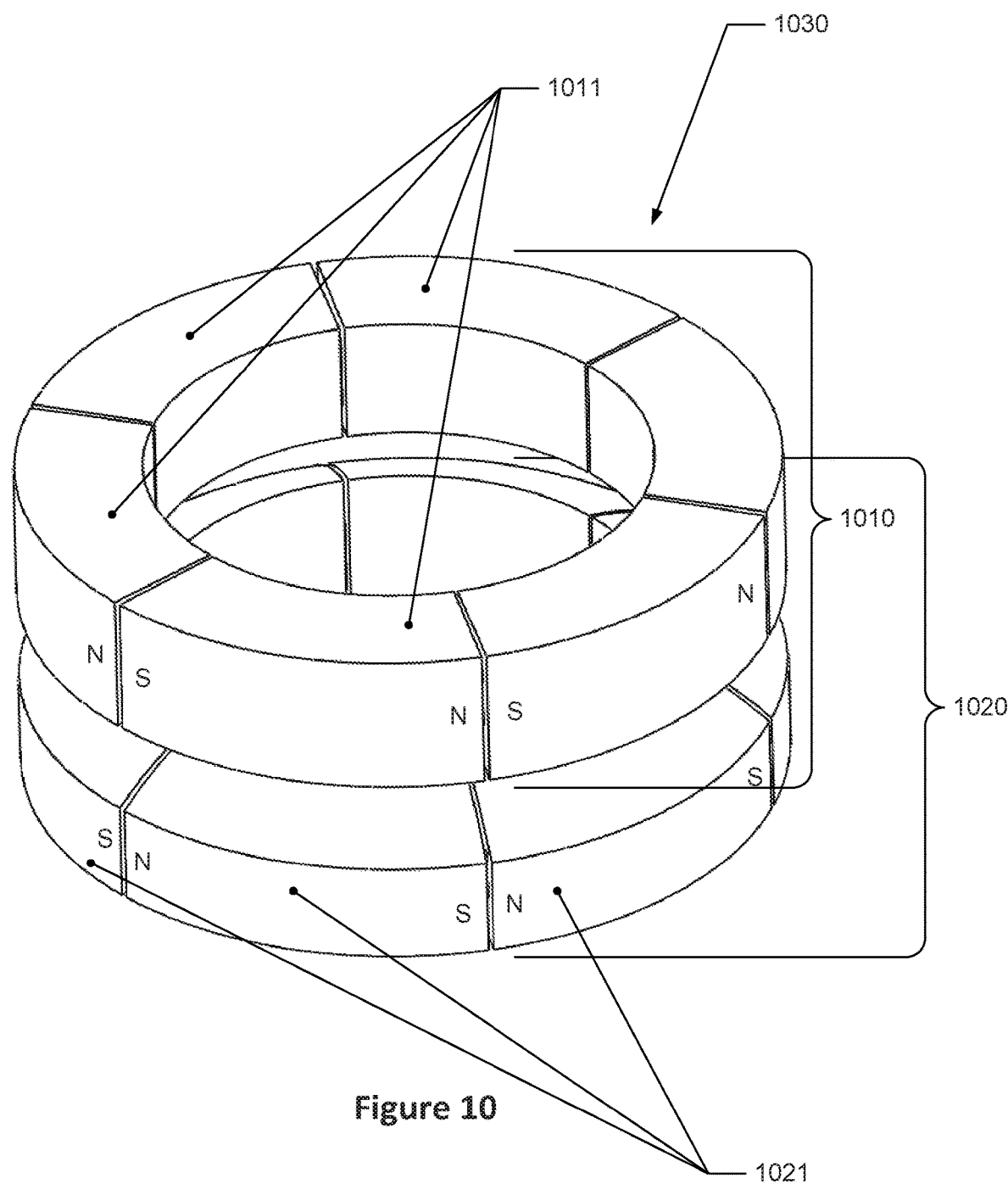
FIG. 10 shows a magnetic member pair featuring segmented magnetic members.

FIG. 10 shows a magnetic member pair 1030 featuring segmented magnetic members. In FIG. 10, a magnetic member pair first magnetic member 1010 and a second magnetic member 1020 are depicted. In this example, each of the first and second magnetic members is divided into six equally sized annular sector shaped segments 1011 and 1021, respectively. Each of the segments 1011 and 1021 may have an opposing magnetic polarity such that the segments of each magnetic member may be magnetically joined end-to-end to form a ring. The polarities of the segments in each magnetic member may be reversed, as shown in FIG. 10, to not only allow the segments of each magnetic member to be joined end-to-end to form a ring, but to allow the two resulting rings to be joined together, as discussed above, to aid in creating an anastomosis.

Magnetic members or segments thereof can be introduced into a patient's body individually. In some cases, magnetic members or segments of magnetic members can be partially assembled when being introduced into a patient's body. In some cases, a magnetic member or segment of a magnetic member can be introduced into a patient's body using an instrument. For example, a magnetic member or segment of a magnetic member can be introduced into a patient's body using the channel of an endoscope, a cannula, a sheath, or the like.

A segment of a magnetic member can be shaped to facilitate assembly (e.g., manual assembly or self-assembly). In some cases, a segment of a magnetic member can be elongated in shape. A segment of a magnetic member can include an elongate, rod-like shape, or an elongate curved shape including a partial annulus, for example. In some cases, a magnetic member can include 2, 3, 4, 5, 6, 7, 8, 9, 10, 11, 12, or more than 12 segments. For example, if an annular magnetic member includes four segments, each segment can be a curved segment including about one quarter of the assembled magnetic member. In some cases, a first segment of a magnetic member can have the same shape or a similar shape as a second segment of the magnetic member. In some cases, a first segment of a magnetic member can have a different shape as a second segment of the magnetic member. A segment of a magnetic member can include an upper surface, a lower surface, or an engagement surface as described herein, and combinations thereof.

The maximum diameter, inner diameter, or outer diameter of a magnetic member can be configured to create an anastomosis of specific dimensions and/or tissue composition. For example varying the difference in magnitude between a magnetic member's inner diameter and outer diameter can affect the amount of tissue being compressed between the engagement surfaces of a first magnetic member and a second magnetic member and can affect the pressure applied to that compressed tissue, leading to different amounts of necrotic tissue in the formed anastomosis. In some cases, the inner diameter of an annular magnetic member can determine the size of the anastomosis that is formed. The radial distance from the inner diameter to the outer diameter of each of the first and second magnetic members (e.g., the radial gap between the inner and outer diameters) can be within a range from about 0.5 mm to about 8 mm, about 1.5 mm to about 8 mm, from about 0.5 mm to about 1.5 mm, from about 1.5 mm to about 2.5 mm, from about 2.5 mm to about 3.5 mm, from about 3.5 mm to about 4.5 mm, from about 4.5 mm to about 5.5 mm, from about 5.5 mm to about 6.5 mm, from about 6.5 mm to about 7.5 mm, from about 7.5 mm to about 8.5 mm, or within a range defined by any two of the preceding values. In some instances, the outer diameter (the maximum dimension) of each member of a magnetic member or magnetic member pair may be no more than about 36 mm, no more than about 30 mm, no more than about 25 mm, no more than about 15 mm, or no more than about 10 mm, no more than about 5 mm, within a range from about 5 mm to about 30 mm, within a range from 10 mm to 25 mm, within a range from about 15 mm to about 20 mm, within a range from about 21 mm to about 23 mm, within a range from about 21.59 mm to about 21.85 mm, within a range from about 21.85 mm to about 23 mm, or within a range defined by any two of the preceding values. In some instances, the outer diameter of a first magnetic member may be within a range from about 8 mm to about 30 mm and the outer diameter of a second magnetic member may be within a range from about 8 mm to about 30 mm. The inner diameter of a magnetic member can be from about 1 mm to about 21 mm, from about 5 mm to about 15 mm, from about 6 mm to about 12 mm, from about 8 mm to about 10 mm, or from about 9 mm to about 12 mm. In some cases, a magnetic member does not have an inner diameter (e.g., a non-annular magnetic member lacking a hole in its center).

The diameters (e.g., inner diameter, outer diameter, and/or maximum diameter) of a first magnetic member can be equal to the corresponding diameters of a second magnetic member, in which the first magnetic member and the second magnetic member make up a magnetic member pair. For example, the first and second inner diameters can be equal. The diameters (e.g., inner diameter, outer diameter, and/or maximum diameter) of a first magnetic member can also be different than the corresponding diameters of a second magnetic member, in which the first magnetic member and the second magnetic member make up a magnetic member pair. For example, the first and second inner diameters can be different.

The magnetic member can include a variety of materials commonly used with implantable devices, including polytetrafluoroethylene (PTFE), polycarbonate, a metal or metallic alloy, a biocompatible non-ferromagnetic material, silicone, or additional biocompatible materials known to one of ordinary skill in the art. The casing for a magnetic material may include one or more of these materials.

The magnetic member typically includes a magnetic material with a magnetic polarity. The magnetic member can be made with the magnetic material (or an alloy thereof), as represented in FIGS. 3A-3F and FIG. 4C, and an optional coating can be provided on the surface. In some instances, a magnetic member can include a magnetic core (e.g., 318 and 328, as in FIG. 3G, FIGS. 5A-5D, FIGS. 6A-6C, and FIG. 8), which includes a magnetic material or magnetic alloy, enclosed in a different material. For example, the first magnetic member 310 may include a first cover 319 enclosing the first magnetic core 318, and the second magnetic member 320 may include a second cover 329 enclosing the second magnetic core 328. The cover many include a biocompatible material known to one or ordinary skill in the art, and may include a casing, a housing or a coating, for example. The magnetic material can include a rare earth element (e.g., neodymium or samarium-cobalt magnets), a ferrimagnetic material, a ferromagnetic material, or a combination thereof. The identity and purity of a magnetic material including a magnetic member can influence the magnetic field generated by the magnetic member.

A first magnetic member 310 of a magnetic member pair 330 can be configured to attract a second magnetic member 320 of a magnetic member pair or vice versa. A first magnetic member 310 (or segments thereof) and a second magnetic member 320 (or segments thereof) of a magnetic member pair 330 can be shaped or selected such that, when the first brought into proximity with one another, they will self-construct (e.g. associate closely and/or engage with one another through mutual magnetic attraction) into a magnetic member pair 330. In some instances, the compressive force generated between the first and second magnetic members is generated by the attractive magnetic force between the first and second magnetic members, which can depend upon the strength of the magnetic field created by each magnetic member and upon the alignment of magnetic polarities between magnetic members. The maximum attractive magnetic force between a first magnetic member 310 and a second magnetic member 320 can be less than or equal to about 50 N, from about 10 N to about 50 N, from about 10 N to about 30 N, from about 5 N to about 50 N, from about 6 N to about 50N, or a range defined by any two of the preceding force values. In some instances, the force (e.g., the attractive magnetic force) is distributed across a substantially flat surface area, although one or more of the engagement surfaces can be curved or inclined relative to the flat surface.

The first magnetic member 310 and the second magnetic member 320 of the magnetic member pair 330 can be shaped to facilitate alignment of the first and second magnetic member when they are engaged with one another (e.g., when they have magnetically associated with one another). For example, the engagement surfaces may include corresponding convex and concave surfaces, or conic surfaces, for example. In some cases, an engagement surface can be roughened, micropatterned, or textured to aid in alignment and/or slippage prevention when a first and second magnetic member of a magnetic member pair are engaged. For example, an engagement surface can be sanded to increase friction during engagement. In some cases, a mold in which the magnetic member or magnetic member casing is made can be shaped such that the engagement surface will include surface features when formed (e.g., micropatterning or texturing). Texturing or micropatterned features of an engagement surface can be on the order of from about 10 micrometers to about 200 micrometers, from about 50 micrometers to about 150 micrometers, from about 50 micrometers to about 100 micrometers, or from about 100 micrometers to about 200 micrometers in any dimension (e.g., height, width, depth, or spacing).

Figure 3A:
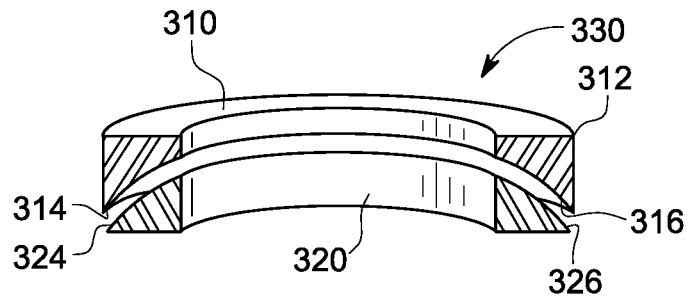
FIG. 3A shows a magnetic member pair in cross-section with unrounded edges and with engagement surfaces including complimentary substantially matched curvatures, in accordance with some implementations.
Figure 3B:
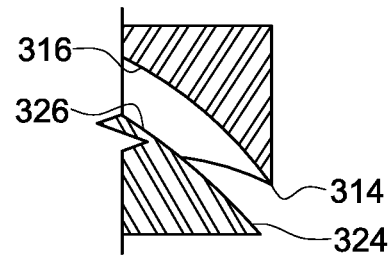
FIG. 3B shows an enlarged view of a magnetic member pair in cross-section as in FIG. 3A.

The engagement surface of a magnetic member can include a curvature. The curvature of the engagement surface can be concave or convex. The engagement surface of a magnetic member can exhibit curvature in a cross-sectional plane passing through a center axis of the magnetic member, e.g., the center axis of an annular magnetic member. As shown in FIG. 3A and FIG. 3B, for example, a first magnetic member 310 of a magnetic member pair 330 can include a first engagement surface 316 that is concave in cross-section and a second magnetic member 320 of a magnetic member pair 330 can include a second engagement surface 326 that is convex in cross-section. In some cases, the engagement surface of a first magnetic member 310 can be substantially flat and the engagement surface of a second magnetic member 320 inclined relative to the engagement surface of the first magnetic member 310 in order to provide a force gradient to tissue when forming the anastomosis.

The cross-section of the engagement surface of a first magnetic member 310 or a second magnetic member 320 can be linear or piecewise linear, or it can include a bevel (e.g., a cross-sectional region with a curvature of zero).

In some cases, the relative cross-sectional curvature and/or angle of the engagement surface (e.g., first engagement surface 316) of a first magnetic member 310 of a magnetic member pair as compared to the curvature and/or angle of the engagement surface (e.g., second engagement surface 326) of a second magnetic member 320 of the magnetic member pair 330 can affect the function of the magnetic member pair. In some instances, (e.g., as shown in FIGS. 3A and 3B), the engagement surfaces of the first and second magnetic members can be configured so that the curvature of the first engagement surface 316 substantially matches the corresponding curvature of the second engagement surface 326, for example with the radii of curvature matching to within about 5 percent. In other cases (e.g., as in FIG. 3C and FIG. 3D), a first magnetic member 310 and a second magnetic member 320 can be configured such that the corresponding curvatures of the first engagement surface and the second engagement surface are not matched by a sufficient amount so as to provide a pressure gradient as described herein.

In some cases, a magnetic member pair including corresponding matched engagement surface curvatures (e.g., first engagement surface 316 and second engagement surface 326, as in FIG. 3A and FIG. 3B) causes the compressive forces between the magnetic members to be distributed over a larger area. In some cases, a magnetic member pair with convex and concave engagement surface shapes can help to align to the first and second magnetic members of the magnetic member pair during engagement of the tissue as described herein. The first and second engagement surfaces may include a protrusion such as a conic protrusion and a channel such as a conic channel shaped to receive the protrusion with the tissue in between.

Figure 3C:
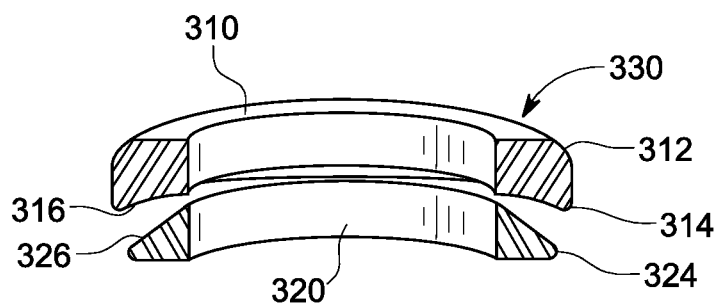
FIG. 3C shows a magnetic member pair in cross-section with rounded edges and with engagement surfaces including corresponding unmatched curvatures, in accordance with some implementations.
Figure 3D:
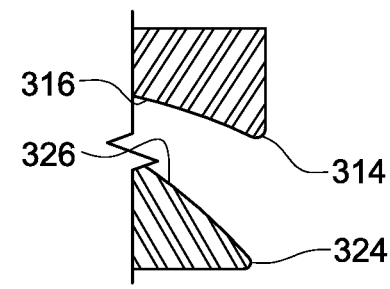
FIG. 3D shows an enlarged view of a magnetic member pair as in FIG. 3C.
Figure 3E:
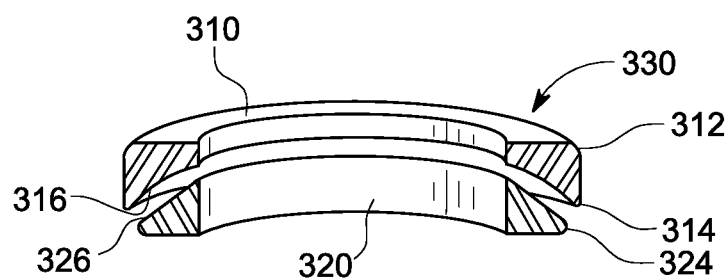
FIG. 3E shows a magnetic member pair in cross-section with rounded edges and with engagement surfaces including corresponding matched curvatures, in accordance with some implementations.
Figure 3F:
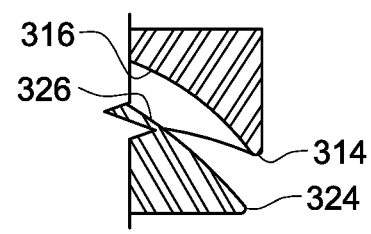
FIG. 3F shows an enlarged view of a magnetic member pair as in FIG. 3E.
Figure 3G:
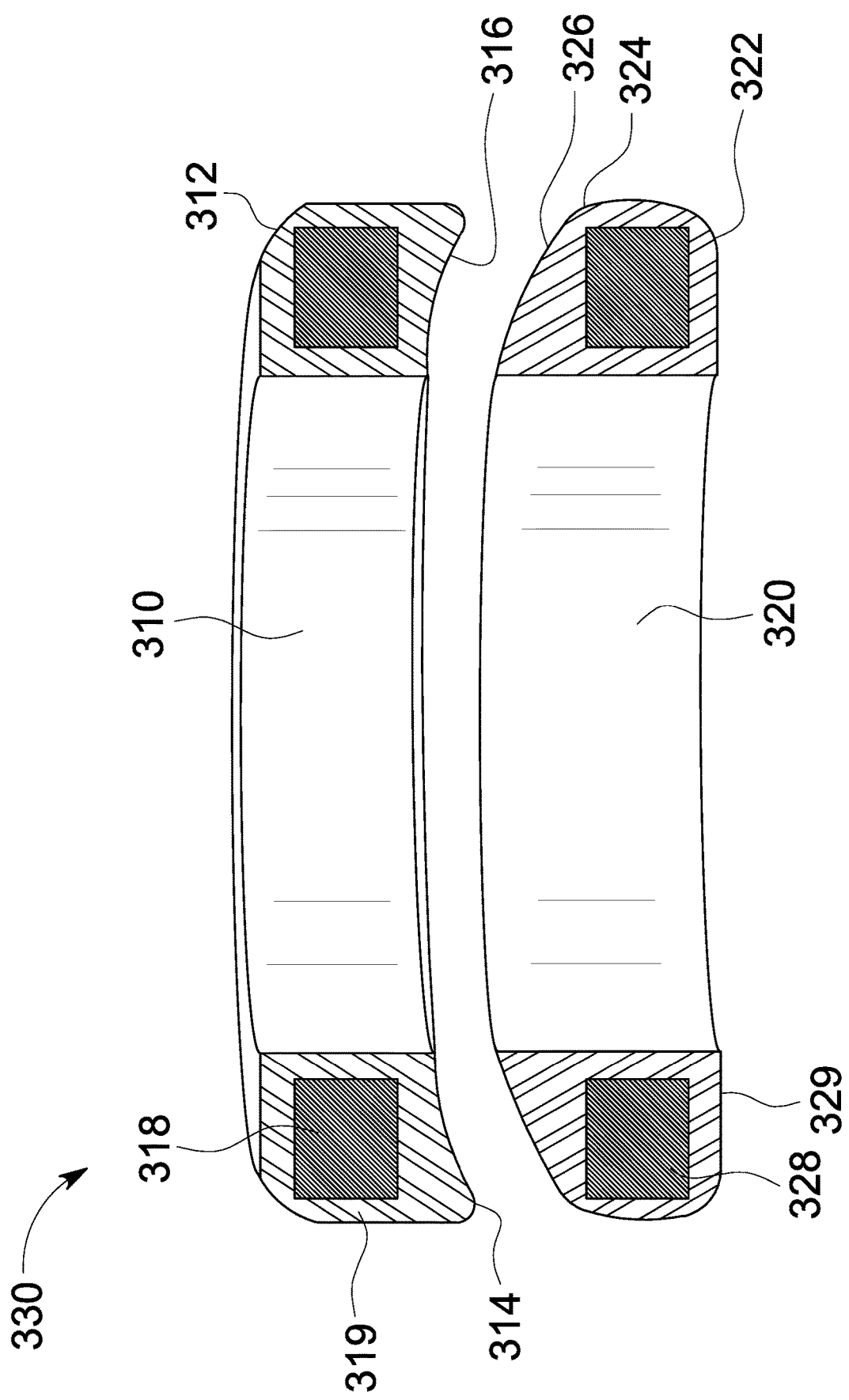
FIG. 3G shows a magnetic member pair in cross-section, with magnetic cores enclosed in a covering including rounded edges, and with engagement surfaces including corresponding matched curvatures, in accordance with some implementations.

When the curvatures of the first and second engagement surfaces (e.g., first engagement surface 316 and second engagement surface 326, as in FIG. 3C and FIG. 3D) include corresponding unmatched curvatures, the pressure gradient across the engagement surfaces of the magnetic members and/or the tissue disposed between the magnetic members of an engaged magnetic member pair 330 can vary along the engagement surfaces. When the curvatures of a first and second engagement surface of a magnetic member pair are unmatched, the pressure gradient across a portion of a magnetic member (e.g., first engagement surface 316 and/or second engagement surface 326) and/or a tissue disposed between the magnetic members of an engaged magnetic member pair, can cause a pressure gradient in a radial direction with respect to the first and/or second surface of a magnetic member (e.g., across the radial length of a surface of a magnetic member, such as across first engagement surface 316 or second engagement surface 326). A pressure gradient across the radial dimension (e.g., the radial length) of a magnetic member or magnetic member pair can extend over a distance of not more than about 10 mm, not more than about 8 mm, not more than about 6 mm, not more than about 4 mm, not more than about 2 mm, not more than about 1 mm, or within a range defined by any two of the preceding values.

The radius of curvature of an engagement surface (e.g., a first engagement surface or a second engagement surface) can be from about 0.200 inches to about 0.800 inches, from about 0.375 inches to about 0.625 inches, from about 0.300 inches to about 0.375 inches, from about 0.375 inches to about 0.450 inches, from about 0.550 inches to about 0.625 inches, or from about 0.625 inches to about 0.700 inches.

Differences in separation distances between first engagement surface 316 and second engagement surface 326 can cause a pressure gradient across a region of the magnetic member and/or across a region of the tissue. The pressure gradient created across a magnetic member, engagement surface, and/or a first and/or second target region (e.g., a first and/or second luminal tissue region) may include a radially inwardly increasing pressure profile. For example, when the engagement surfaces include corresponding unmatched curvatures, a different pressure can be exerted on the outer portion of a magnetic member engagement surface or on a tissue region disposed between the engagement surfaces of a first and second magnetic member of a magnetic member pair than on the inner portion of a magnetic member engagement surface or on a tissue region disposed between the engagement surfaces. The different pressures exerted on the engagement surface(s) or tissue region(s) can include a pressure gradient (e.g., a radial pressure gradient).

The pressure exerted on the radially inward portions of the first and a second luminal tissue target regions can be greater than the pressure exerted on the radially outward portions of the first and second luminal tissue target region by a factor of at least 1.5, at least 2, at least 2.5, at least 3, at least 3.5, at least 4, at least 4.5, at least 5, at least 6, at least 7, at least 8, at least 9, or at least 10. The pressure exerted on inner portions of a first and a second luminal tissue target regions can be greater than the pressure exerted on the outer portions of the first and second luminal tissue target region by a factor between 1-fold and 2-fold, a factor from 2-fold to 3-fold, a factor from 3-fold to 4-fold, a factor from 4-fold to 5-fold, a factor from 5-fold to 7.5 fold, or a factor from 7.5-fold to 10-fold. The pressure exerted on the first and second engagement surfaces of the magnetic member pair and the first and second luminal tissue target region can be less than 100 kPa. In some instances, pressure exerted on the first engagement surface, the second engagement surface, the first luminal target tissue region, and the second luminal tissue target region can range from about 5 to 15 kPa, from about 15 to 25 kPa, from about 25 to 35 kPa, from about 25 to 45 kPa, from about 25 to 53 kPa, from about 25 to 55 kPa, from about 35 to 45 kPa, from about 45 to 55 kPa, from about 55 to 65 kPa, from about 65 to 75 kPa, from about 75 to 85 kPa, from about 85 to 95 kPa, or from about 95 to 100 kPa. Optionally, the pressure exerted on the outer surface of a magnetic member or the outer portion of a first and second luminal tissue target region can range from about 2 kPa to about 12 kPa, from 2 kPa to 10 kPa, from 2 kPa to 8 kPa, or from 2 kPa to 5 kPa. As described herein, the pressure exerted may refer to a pressure exerted by the magnetic pair within 4 hours, 3 hours, 2 hours, 1 hour, 30 minutes, 15 minutes, or 1 minute of engagement of the magnetic members or magnetic member pair(s). The pressure exerted on a tissue disposed at a location between a first magnetic member 310 and a second magnetic member 320 can increase or decrease over time (e.g., as the tissue remodels and necrotizes as a result of the application of the magnetic member pair).

The difference between the pressure exerted on the inner portion of the engagement surface of a magnetic member and the pressure exerted on the outer portion of the engagement surface of the magnetic member can decrease over time (e.g., after the first and second magnetic members have been attracted to each other and/or engaged with one another. The pressure exerted on an outer engagement surface of the magnetic member (e.g., the outer surface of a magnetic member or the engagement surface of a magnetic member) can increase over time. The increase in pressure on the outer portion of the engagement surface of a magnetic member can be due to necrosis of tissue contacting the magnetic member (e.g., tissue disposed between the outer portions of the engagement surfaces of the magnetic members). The pressure exerted on the inner portion of a first and/or second magnetic member (e.g., the inner portion of the engagement surface(s) of a first and/or second magnetic member) after the magnetic members of a magnetic member pair are initially engaged through magnetic attraction can be above a threshold pressure to effect necrosis in a portion of biological tissue disposed between the inner portions of the magnetic members (e.g., the inner portions of the engagement surfaces of the magnetic members). The pressure exerted on the outer portion of a first and/or second magnetic member (e.g., the outer portion of the engagement surface(s) of a first and/or second magnetic member) after the first and second magnetic member have been brought together (e.g., after the first and second magnetic member first engaged one another via magnetic attraction) can be below a threshold pressure to effect necrosis in a tissue disposed between the outer portions of the first and second magnetic members (e.g., between the outer portions of the first and second magnetic members' engagement surfaces). The pressure on the outer portions of the engagement surfaces of the magnetic members can increase above a threshold pressure sufficient to induce or effect necrosis in the tissue.

Differences in pressure distribution experienced by a tissue disposed between an engaged magnetic member pair can affect the biological effect that the compressive force between magnetic members have upon the tissue that is disposed between them. For example, if the pressure is too high an increase in pressure on a tissue can cause potentially undesirable cutting of the tissue rather than compressive anastomosis with necrosis and healing of the tissue target region. The engagement surfaces as described herein can, in some implementations, provide anastomosis without cutting tissue with forces between 6 N and 15 N or between 1 N and 15 N. If the engagement surfaces (e.g., first engagement surface 316 and second engagement surface 326) of the first and second magnetic members are unmatched, i.e., have a separation gap between them that varies radially, compression of a tissue between the first and second magnetic member can cause necrosis with healing of tissue so as to fuse tissue of the first target region with tissue of the second target region. With the pressure gradients as described herein, portions of tissue engaged with radially inward portions of the engagement surfaces preferentially necrotize prior to outer portions of the engagement surfaces. As the inner portions of tissue necrotize at each of the first and second target sites, these tissues become weakened, and the magnetic members move closer to each other. This movement of the magnetic members toward each other increases the amount of pressure applied to radially outward portions of tissue between the engagement surfaces, which in turn, necrotize. The necrosis continues until a sufficiently large portion of tissue has necrotized to allow passage of the magnetic members through the anastomosis and into the bowel or other lumen. The presence and spatial distribution of a pressure gradient across a tissue (e.g., through application of a magnetic member pair to the tissue) can also affect the degree and geometry of remodeling, and/or necrosis that result from the tissue experiencing the pressure gradient.

Differences in pressure distribution (e.g., a pressure gradient) experienced by a tissue disposed between an engaged magnetic member pair can affect the speed at which an anastomosis forms. For example, increased pressure can cause tissue to form an anastomosis more quickly. The engagement surfaces as described herein can be configured provide necrosis over an amount of time as described herein so as to allow healing and fixation of the first target region to the second target region with increased amounts of force, for example greater than 6 N.

The pressure distribution experienced by a tissue compressed between magnetic members of an engaged magnetic member pair can be affected by the dimensions (e.g., thickness) and/or mechanical properties of the tissue disposed between or adjacent to the magnetic members of the magnetic member pair. For example, the modulus of compression and viscoelasticity of a tissue (e.g., a first and/or second target region) disposed between a first and second magnetic member can affect the speed and biological effect of compression on the tissue. Heterogeneities in the mechanical properties of the tissue can also affect the spatial pressure distribution experienced by the tissue. For example, a first region of tissue disposed between a portion of an engaged magnetic member pair that has a higher modulus of compression than other regions of the tissue disposed between the same engaged magnetic member pair can affect the pressure distribution in those other regions of tissue disposed between the magnetic member pair. The magnetic members of the magnetic member pair can be configured to compensate for the mechanical properties of a first and/or second target region in order to create a desired pressure distribution profile in the first and/or second target regions with increased amounts of force that allow one type of magnetic member pair to be used with several types of gastrointestinal anastomoses and many different types of people, e.g., of varying weight, size and age, for example.

The cross-sectional curvature of an engagement surface can also affect the type and/or speed of anastomosis formation. The cross-sectional curvature of the engagement surface can be configured according to the desired effects of the magnetic pair.

The magnetic members as described herein may include rounded edges (e.g., first engagement edge 314, second engagement edge 324, first outer edge 312, and/or second outer edge 322), which can decrease resistance to sliding movement and decrease damage to tissue when the magnetic member is engaged with a magnetic placement instrument through the luminal wall as described herein. The rounded edge can be sufficiently small so as to allow the formation of an anastomosis having a maximum cross-sectional size (e.g., diameter) greater than the maximum cross-sectional dimensions of each member of the magnetic member pair, while also allowing decreased tissue pressure at the edges of the magnetic members. In some instances, the radius of curvature of an edge of a magnetic member can be less than about 0.01 mm, from about 0.01 to about 0.05 mm, from about 0.05 mm to about 0.1 mm, from about 0.127 mm to about 0.150 mm, from about 0.1 to about 0.2 mm, from about 0.2 mm to about 0.5 mm, from about 0.5 mm to about 1 mm, from about 1 mm to about 5 mm, or from about 5 mm to about 10 mm. The radius of an edge of a magnetic member can also be from about 0.001 inches to about 0.020 inches, from about 0.001 inches to about 0.005 inches, from about 0.005 inches to about 0.010 inches, from about 0.010 inches to about 0.020 inches. Although reference is made to a radius of curvature, the edges can be rounded in many ways, such as with piecewise linear segments, elliptical and other geometries. In general, the rounded edge can be configured such that a tangent line extending radially outward along the engagement surface undergoes a rotation within a range from about 45 to about 135 degrees over a distance within a range from about 0.01 mm to 0.75 mm, from about 0.02 mm to about 0.5 mm, or from about 0.05 mm to about 0.25 mm, for example. Alternatively or in combination, the edge of a magnetic member can be unrounded (e.g., an edge of a magnetic member can include the curvilinear intersection of two surfaces in which the surfaces do not form a continuous curve in cross-section at the point of intersection). In some cases, the edge of a magnetic member can include a fillet, a chamfer, or a bevel.

The shape of the edges (e.g., first engagement edge 314 or second engagement edge 324) of the first magnetic member 310 and second magnetic member 320 can influence the effect an engaged magnetic member pair has on a tissue disposed between the magnetic members. For instance, a rounded edge (e.g., first engagement edge 314 and second engagement edge 324 as in the implementations depicted in FIG. 3C, FIG. 3D, FIG. 3E, and FIG. 3F) can promote sliding and inhibit damage (e.g., abrasion or laceration) to biological tissue that contacts the edge as compared to an unrounded or sharp edge (e.g., first engagement edge 314 and second engagement edge 324, as in FIGS. 3A and 3B). The extent to which the edges are rounded can depend on the placement instrument used, and it is contemplated that sharp edges can be used in accordance with some implementations.

Figure 8:
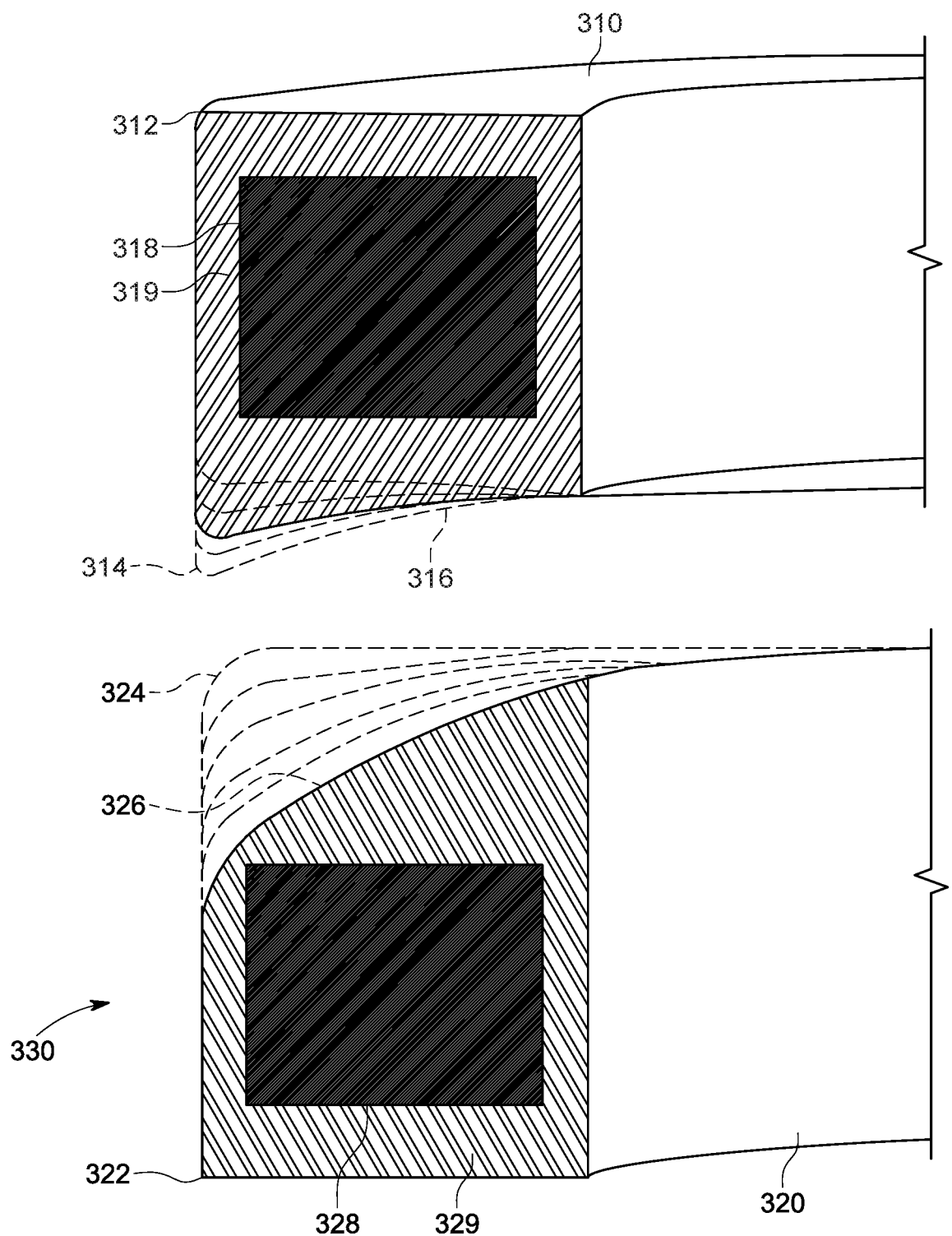
FIG. 8 shows a schematic diagram of engagement surfaces of a magnetic member pair and coverings over magnetic cores, in accordance with some implementations.

FIG. 8 shows a schematic diagram of implementations of the engagement surfaces of an upper magnetic member (e.g., a first magnetic member 310) and a lower magnetic member (e.g., a second magnetic member 320) of a magnetic member pair 330, in which the angle of the engagement surface (see first engagement surface 316 and second engagement surface 326), relative cross-sectional angle of curvature, absolute cross-sectional curvature, degree of edge rounding (see first outer edge 312 and second outer edge 322) can each be varied independently or in proportion in the upper magnetic member relative to the lower magnetic member. In general, the complementary surfaces are configured to provide a desired separation distance to provide an appropriate tissue pressure gradient as described herein. Magnetic member engagement edges (e.g., first engagement edge 314 and/or second engagement edge 324) can be rounded or unrounded as well, either independently or to the same or similar degree in one magnetic member of a magnetic member pair compared to the other magnetic member of the magnetic member pair.

While each of the magnetic members, such as first magnetic member 310 and second magnetic member 320, may include a single part configured for insertion into the patient, the magnetic member may include a plurality of segments configured for in situ assembly within the patient and can be configured similarly to the first and second magnetic members as described herein. The segments of a plurality of segments can be movable relative to one another for insertion through a laparoscope as is known to one of ordinary skill in the art. Once introduced into the lumen, the segments of the plurality of segments can be arranged within the patient's lumen to form the magnetic member. For example, the segments of a plurality of segments including a magnetic member can self-construct (e.g., self-assemble or associate with one another to form a magnetic member or a portion of a magnetic member) through mutual magnetic attraction.

The segments of a magnetic member can be introduced into the body individually or in an unassembled, narrow profile configuration. In some cases, the segments of a magnetic member can be introduced into the body in a partially assembled configuration. Each segment of a magnetic member can be elongate, e.g., rod-like or curved in shape, and assembled within the patient's lumen outside of the endoscope, for example. In some cases, a segment of a magnetic member can be shaped to facilitate introduction into the body within a lumen of a surgical device such as a laparoscope or an endoscope, for example. The introduction of a segment of a magnetic member into the body can be accomplished by advancing the segment along a lumen of the surgical instrument in a narrow profile configuration with the segments connected or unconnected. Introduction of a magnetic member and/or segments of a magnetic member can include introducing a magnetic member and/or a segment of a magnetic member individually and sequentially. In some cases, introduction of a magnetic member and/or segments of a magnetic member can include introducing each segment of a plurality of segments of a magnetic member at different times into a lumen of an endoscope, for example.

Magnetic Member Placement Instrument

Referring to FIGS. 4A-4C, a placement instrument 110 can include a proximal end, a handle 112 at the proximal end, a distal end 116, and an elongate member 114 (e.g., a shaft) disposed between the handle and the distal end. The elongate member 114 can have a distal portion and a proximal portion. The handle can include a shaft and can be configured to be grasped by a user. The distal end 116 of an elongate member 114 can be rounded or unrounded, and it can include a concave surface or a convex surface, for example. In some cases, the shape (e.g., the convexity or concavity) of the distal end 116 of a placement instrument can be designed or selected to be complementary to a given magnetic member in order to aid in installation, positioning, manipulation, or retrieval of the magnetic member. The distal end of the placement instrument (e.g., distal end 116) can have a substantially flat surface with rounded edges. The edges of the distal end 116 of a placement instrument 110 can be rounded in order to promote sliding of the distal end around tissue and to inhibit damage (e.g., incision, perforation, laceration, or abrasion) to a biological tissue that contacts the distal end 116 of the placement instrument 110. The distal end 116 of the placement instrument can be rounded to engage the magnetic member with decreased pressure. The placement instrument with a rounded distal end 116 can exert decreased pressure on a portion of tissue (e.g., a luminal wall) disposed between the distal end 116 of the placement instrument 110 and the magnetic member compared to an unrounded end.

The placement instrument 110 can be configured to be used to guide the magnetic member along a portion of the gastrointestinal tract of a patient in order to place the magnetic member at a target location (e.g., a target region of the gastrointestinal tract). The placement instrument 110 including a rounded distal end 116 can decrease the pressure on tissue disposed between the placement instrument and the magnetic member (e.g., a luminal wall of a gastrointestinal tract) as the placement instrument 110 guides the magnetic member to a target area as described herein.

The elongate member 114 of a placement instrument can be flexible or stiff, or combinations thereof (e.g., stiff or rigid in the handle portion, and flexible in the distal portion), and can be sized to manipulate the magnetic member placed in the patient's lumen from outside the patient. The elongate member 114 may be no more than about 50 cm in length, equal to or more than 50 cm in length, between 50 cm and 120 cm in length, between 60 cm and 100 cm in length, between 70 and 90 cm in length, or between 75 and 85 cm in length. In some instances, the handle 112 can be located at the proximal end 113 of the elongate member. In some cases, the length of the handle 112 and the elongate member 114 (e.g., an elongate shaft) may be equal to or more than 50 cm in length, from about 50 cm and 60 cm in length, from about 60 cm to about 70 cm in length, from about 70 cm to about 80 cm in length, from about 80 cm to about 90 cm in length, from about 90 cm to about 100 cm in length, no more than about 100 cm in length, from about 100 cm in length to about 110 cm in length, from about 110 cm in length to about 120 cm in length, or within a range defined by any two of the preceding values.

The placement instrument 110 (e.g., an insertion or retrieval instrument) can be rounded in cross-section (e.g., circular or oval in cross-section) or it can be polygonal in cross-section, for example. A cross-sectional dimension of a placement instrument 110 (e.g., a cross-sectional width of a placement instrument) may be no more than 15 mm, no more than 12 mm, no more than 10 mm, no more than 9 mm, no more than 8 mm, no more than 7 mm, no more than 6 mm, no more than 5 mm, no more than 4 mm, no more than 3 mm, no more than 2 mm, no more than 1 mm, about 0.01 mm to about 15 mm, about 1 mm to about 12 mm, about 2 mm to about 10 mm, about 4 mm to about 8 mm, or about 5 mm to about 6 mm. The cross-sectional dimension (e.g., diameter) of the elongate member 114 of the placement instrument can be substantially fixed along a majority of the length of the elongate member 114. The cross-sectional dimension (e.g., diameter) of the elongate member of a placement instrument can vary along a substantial length of the elongate member 114.

The placement instrument 110 may include a magnetic material 118. The magnetic material 118 can include iron, a magnetic rare earth element, a magnet, or combinations thereof. The magnetic material can be located at the distal end 116 of the placement instrument 110, as exemplified in FIG. 4B, and it can be encased in the material including the shaft of the placement instrument or another material. The magnetic material of the placement instrument can generate a magnetic field (e.g., as in FIG. 4C). The magnetic field of the magnetic material of the placement instrument can be aligned with the magnetic field of a magnetic member (e.g., as in FIG. 4C), and the magnetic member and the magnetic material of the placement instrument can exert a magnetic attractive force upon one another. Although the magnet located on the distal end portion may include a non-magnetized magnetic material, a magnet or magnetized material located on the distal end portion of the placement instrument can appropriately orient the first magnetic member 310 or the second magnetic member 320 to the placement instrument in order to facilitate manipulation and placement.

The magnetic force between the placement instrument and a magnetic member may generally be no more than 6 N, no more than 5 N, no more than 4 N, no more than 3 N, nor more than 2 N, or no more than 1 N, no more than 0.5 N, no more than 0.25 N, within a range from about 0.01 N to about 4 N, from about 0.1 N to about 2N, or from 0.01 N to 6 N, in order to allow manipulation of the magnetic member through the intestinal wall for placement at the target location and to allow the magnetic member to be readily separated from the placement instrument when appropriate. The distal end portion of the placement instrument and the magnetic member may be shaped and configured so as to cause the magnetic member and the distal end portion of the placement instrument to work together so as to engage the magnetic member with an appropriate amount of pressure to the tissue, such as less than 50 kPa, less than 40 kPa, less than 30 kPa, less than 20 kPa, or less than 10 kPa, for example. In some cases, the magnetic material of a placement instrument can include a shape complementary to that of a magnetic member.

Together, the placement instrument 110, a first magnetic member 310 of a magnetic member pair (e.g., an upper magnetic member), and a second magnetic member 320 of a magnetic member pair 330 (e.g., a lower magnetic member) can include a system for forming an anastomosis (an implementation of such a system is depicted in FIGS. 5A-5D, for example). A system for forming an anastomosis can further include a second instrument. A second instrument of a system for forming an anastomosis can be a second placement instrument (an implementation of such a system is depicted in FIGS. 6A-6C, for example). A second instrument of a system for forming an anastomosis can be used to guide a second magnetic member towards a target location. The target location can be near a first magnetic member 310. A second instrument can be used to physically manipulate a tissue or organ so that it is in proximity to another tissue or organ. For example, a second target region of the gastrointestinal tract can be physically manipulated by a second instrument (e.g., a surgical tool) so that it is in close proximity to a first target region of the gastrointestinal tract. Such manipulation of a tissue or organ with a second instrument can be performed to bring a first and a second magnetic member into close proximity to engage the first and second magnetic member with one another through magnetic attraction. The placement instrument can be used to retrieve a magnetic member from a patient's body.

Manipulation of a Magnetic Member with Placement Instrument

FIGS. 5A-5D show a method for coupling magnetic members of a magnetic member pair to generate an anastomosis, in accordance with some implementations. The placement instrument 110 can interact with a magnetic member such as first magnetic member 310 in order to place the magnetic member at the target location, such as a location within the alimentary canal of a patient. The placement instrument 110 can be used to place the second magnetic member 320 at the second target location, and then used to position the first magnetic member 310 at the first target location. Alternatively, a plurality of placement instruments can be used as described herein.

Figure 5A:
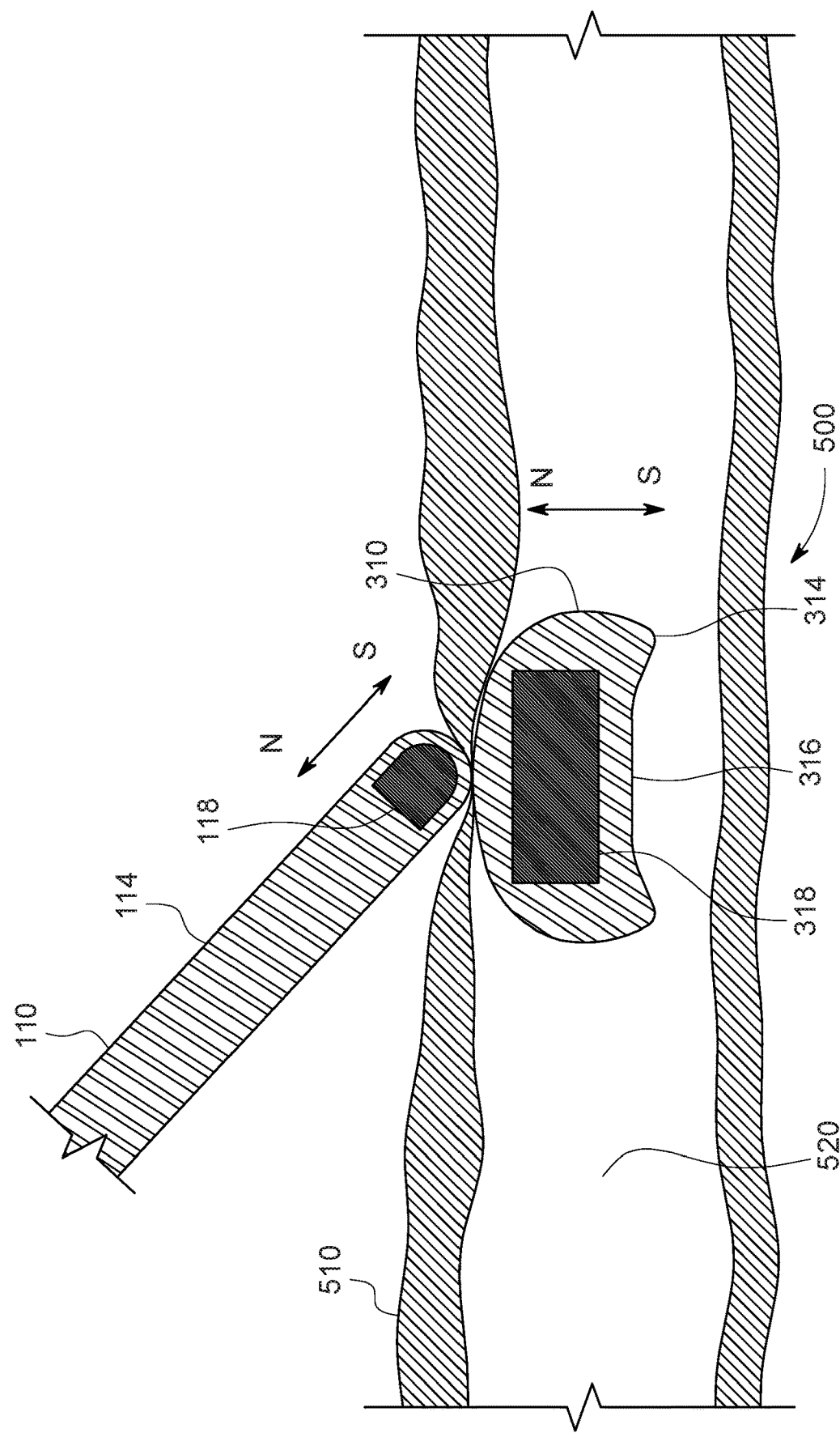
FIG. 5A shows a step of engaging a magnetic member with a placement instrument, in accordance with some implementations.
Figure 6A:
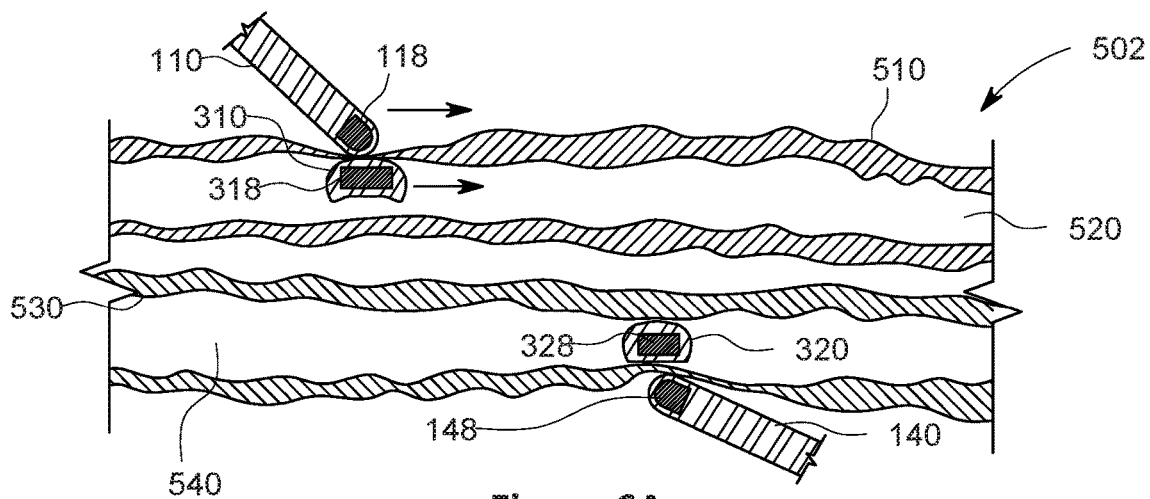
FIG. 6A shows a step of manipulating a first magnetic member using a first placement instrument and manipulating a second magnetic member using a second placement instrument, in accordance with some implementations.
Figure 6B:
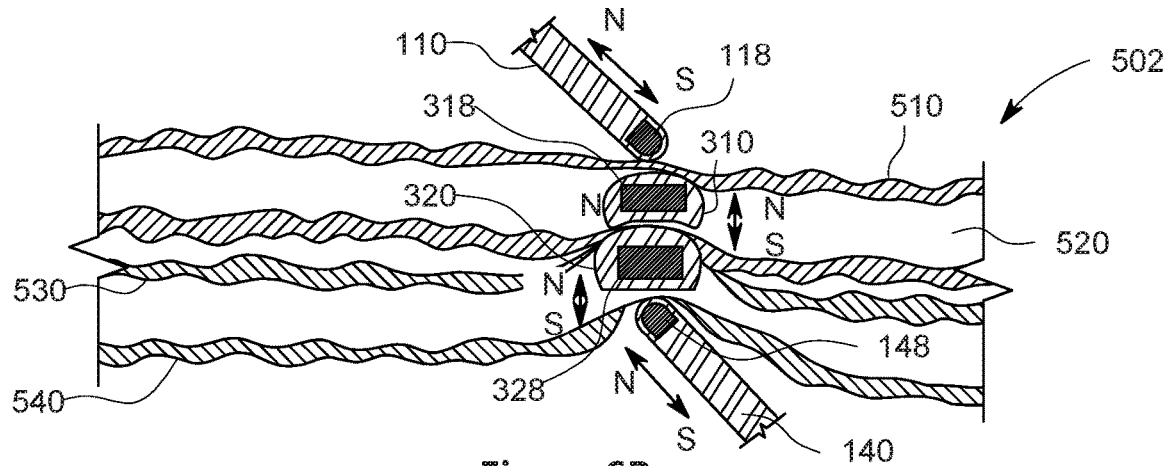
FIG. 6B shows a step of engaging a first magnetic member with a second magnetic member during using first and second placement instruments, in accordance with some implementations.
Figure 6C:
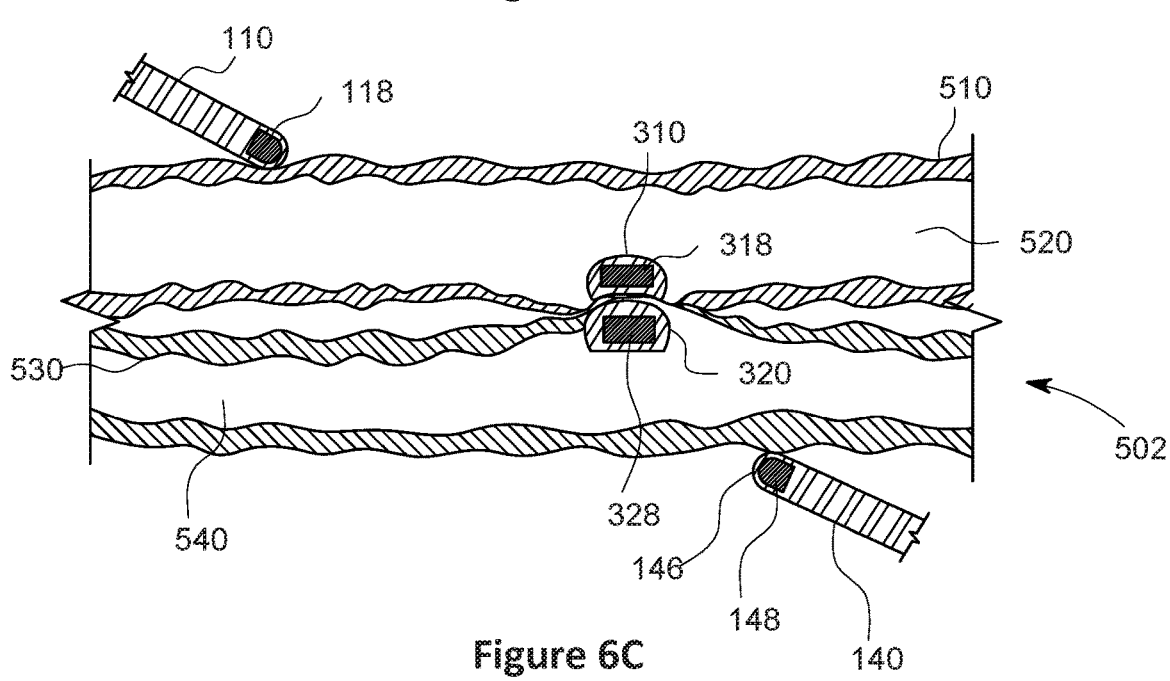
FIG. 6C shows a step of disengaging and retracting a first placement instrument and a second placement instrument following engaging a first magnetic member and a second magnetic member, in accordance with some implementations.

The placement instrument 110 can be configured to interact with the first magnetic member 310 in the body, as exemplified in FIG. 5A, which references a step of a method for coupling the magnetic members of a magnetic member pair to form an anastomosis at target site 500 including the first target location of the first tissue and the second target location of the second tissue. A magnetic member as described herein, which can include a magnetic material (e.g., a magnetic core 318), an engagement edge (e.g., first engagement edge 314 or second engagement edge 324), and an engagement surface (e.g., first engagement surface 316 or second engagement surface 326), can be placed within a cavity of the body (e.g., within the lumen of a tubular structure, such as a region of the small intestine). The tubular structure can include a luminal wall 510 defining an inner or first lumen 520.

The shape, size and magnetic properties of the placement instrument 110 can be selected and configured based on the shape, size and magnetic properties of the magnetic member with which it is intended to be used in order to provide better control in manipulating and placing the magnetic member. For example, the placement instrument 110 can include a rounded distal end portion in order to decrease the surface area in compressive contact with the magnetic member (e.g., with a biological tissue disposed between the placement instrument and the magnetic member). The placement instrument, which can include magnetic material 118, can be advanced into close proximity with the magnetic member, causing the placement instrument and the magnetic member to interact through the luminal wall 510. The interaction between the placement instrument 110 and the magnetic member may include magnetic attractive forces resulting from mutual attraction between the magnetic material of the placement instrument and the magnetic material of the magnetic member. In some instances, the placement instrument can contact the magnetic member (e.g., to install, to manipulate, to position, or even to retrieve the magnetic member if appropriate).

The placement instrument 110 can be configured to interact with a magnetic member across a biological tissue (e.g., a tissue of a region of a body cavity, such as an luminal wall 510) that is disposed between the placement instrument and the magnetic member. The placement instrument 110 (e.g., the distal end 116 of the placement instrument 110) and/or the magnetic member (e.g., the outer surface of the magnetic member) can be in contact with the biological tissue (e.g., a luminal wall 510 enclosing the first lumen 520). The biological tissue typically contacts the placement instrument 110 and the magnetic member when the placement instrument and the magnetic member are engaged with one another. A biological tissue disposed between a placement instrument and a magnetic member can be compressed during engagement of the placement instrument 110 and the magnetic member with a force of no more than 6 N, no more than 5 N, no more than 4 N, no more than 3 N, no more than 2 N, no more than 1 N, no more than 0.5 N, no more than 0.25 N, and the amount of force can be within a range defined by any two of the preceding values, for example.

Figure 5B:
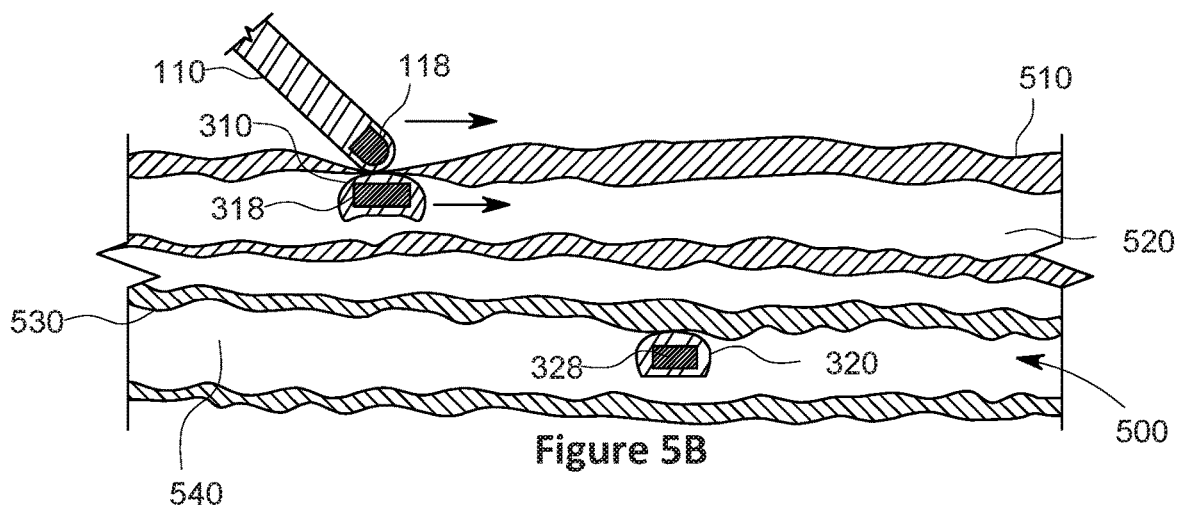
FIG. 5B shows a step of placing a magnetic member at a target location with a placement instrument, in accordance with some implementations.

FIG. 5B shows a step of sliding a magnetic member to a target tissue location where an anastomosis is to be formed. The placement instrument 110 engages the magnetic member through the luminal wall 510 disposed between the placement instrument 110 and the first magnetic member 310 or the second magnetic member 320 without requiring piercing of the luminal wall 510. The placement instrument 110 thus engaged with a magnetic member can be used to slide the magnetic member along a distance along the luminal wall to position the magnetic member in close proximity to the target region where the anastomosis is to be formed. The placement instrument 110 and magnetic member can be slid along, a section of a gastrointestinal tract without substantially abrading or incising tissue of the patient along which the placement instrument and magnetic member slide.

A target region can be determined with reference to a specific anatomical location, such as a distance from the ileocecal valve or the pyloric sphincter, for example. The first and second target locations can be brought into proximity with each other using known surgical tools such as forceps, for example. The second magnetic member can be placed at the second target location before the first magnetic member is placed at the first target location, and the first magnetic member can be slid along the luminal wall so as to engage the second magnetic member, for example. As one of ordinary skill in the art will appreciate, the order can be reversed. In some instances, the placement instrument 110 and associated magnetic member can be slid along the luminal wall any appropriate distance. For example, when the lumen includes the alimentary canal, the distance can be within a range, for example a distance within a range from about 0.1 to about 6 meters.

The attractive force between the magnetic material of the placement instrument 110 and a first magnetic member 310 or the magnetic core of a first magnetic member 310 (or the second magnetic member 320 or the magnetic core of the second magnetic member 320) can be less than the attractive force between a first magnetic member 310 and a second magnetic member 320 in order to allow separation of the placement instrument from the first magnetic member and the second magnetic member when coupled to each other. The placement instrument can be used to position a second magnetic member such that it engages with a first magnetic member 310 and then disengage the second magnetic member 320 without dislodging or disengaging the second magnetic member 320 from the first magnetic member 310.

The engagement of the placement instrument 110 with the magnetic member (e.g., a first magnetic member 310 or a second magnetic member 320) can include sufficient interaction between the placement instrument 110 and the magnetic member (e.g., through magnetic attraction) that the placement instrument 110 can be used to slide, manipulate, or position the magnetic member with which it is engaged with a portion of tissue is disposed between the placement instrument 110 and the magnetic member The forces, pressures, and or durations of engagement between the placement instrument 110 and a magnetic member can be configured to promote sliding of the magnetic member and are generally not sufficient to cause damage to (e.g., necrosis, cutting, or laceration). of the portion of tissue disposed between the placement instrument 110 and the magnetic member. Each of the magnetic members and the distal portion of the placement instrument may include sufficiently smooth surfaces so as to allow the distal portion and each of the magnetic members to be slid along the intestinal wall, for example.

Figure 5C:
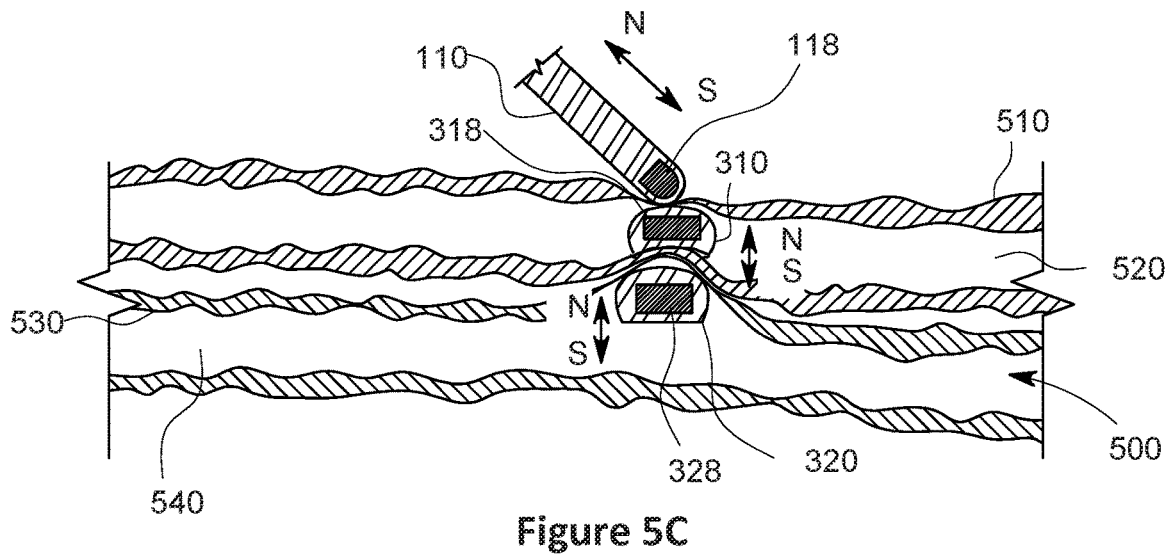
FIG. 5C shows a step of engaging a first magnetic member with a second magnetic member, in accordance with some implementations.

FIG. 5C is now referenced, which shows coupling the magnetic members of a magnetic member pair to create an anastomosis at target site 500. The placement instrument 110 can be used to position a first magnetic member 310 in a first region (e.g., a first target region) of the gastrointestinal tract in close proximity to a second magnetic member 320, which can be disposed within a second region (e.g., a second target region) of the gastrointestinal tract. The first magnetic member 310 and the second magnetic member 320 can be separated by at least a tissue wall (e.g., a tissue wall of the gastrointestinal tract of a patient). The positioning of a first magnetic member 310 relative to a second magnetic member 320 can result in the first magnetic member 310 engaging the second magnetic member 320. The placement instrument can be used to manipulate the first magnetic member 310 in order to align the magnetic field of the first magnetic member 310 with the magnetic field of the second magnetic member 320. The manipulation of a first magnetic member 310 relative to a second magnetic member 320 can cause the first magnetic member 310 to engage the second magnetic member 320. The attractive magnetic force can cause a first magnetic member 310 to engage with a second magnetic member 320, and the magnetic attractive force can be caused by the interactions of the magnetic field produced by the magnetic material of the first magnetic member 310 and the magnetic field produced by the second magnetic member 320 (e.g., when the magnetic field of the first magnetic member 310 is aligned with the magnetic field of the second magnetic member 320).

The attractive magnetic force between the first magnetic member 310 and the second magnetic member 320 can be greater than or equal to the attractive magnetic force between the placement instrument and a first magnetic member 310 (which can be caused by the interaction of the magnetic field produced by the magnetic material of the placement instrument and the magnetic field produced by the magnetic material of the first magnetic member 310). The interactive force (e.g., the attractive magnetic force) between the magnetic member and a placement instrument 110 can be within the ranges and values described herein, for example less than 0.01 N, from about 0.01 N to about 4 N, from about 0.1 N to about 2 N, from about 0.01 N to about 1 N, from about 0.1 N to about 1 N, from about 1 N to about 2 N, from about 2 N to about 3 N, from about 3 N to about 4 N, from about 4 N to about 5 N, from about 5 N to about 6 N, no more than 0.1 N, no more than 0.5 N, no more than 1 N, no more than 1.5 N, no more than 2 N, no more than 2.5 N, no more than 3 N, no more than 4 N, no more than 5 N, or no more than 6 N. The pressure between the placement instrument and a magnetic member can be within a range from about 5 kPa to about 10 kPa, from about 10 kPa to about 15 kPa, from about 10 kPa to about 20 kPa, from about 20 kPa to about 30 kPa, from about 30 kPa to about 40 kPa, from about 40 kPa to about 50 kPa, no more than about 50 kPa, no more than about 40 kPa, no more than about 30 kPa, no more than about 20 kPa, or no more than about 10 kPa. In some instances, the attractive magnetic force between a first magnetic member 310 and a second magnetic member 320 may include an amount and/or range as described herein, for example at least about 6 N, at least 10 N, at least 15 N, at least 20 N, within a range from about 3 N to about 30 N, from about 6 N to about 20 N, from about 6 N to about 15 N, or from about 1 N to about 15 N.

The compressive force experienced by the tissue disposed between the first and second magnetic members when they engage one another generally includes an amount of force as described herein, and can be at least about 1N, at least about 6 N, at least 10 N, at least 15 N, at least 20 N, no more than 50 N, from about 10 N to about 50 N, from about 10 N to about 30 N, from 6 N to 10 N, from 10 N to 15 N, or from 15 N to 20 N, from 20 N to 30 N, from 30 N to 40 N, from 40 N to about 50 N, or within a range defined by any two of the preceding values.

The engagement of a first magnetic member 310 disposed in a first region of the alimentary canal and a second magnetic member 320 in a second region of the alimentary canal can result in necrosis of the tissue disposed between the first and second magnetic members so as to form an anastomosis as described herein. The engagement of a first magnetic member 310 disposed in a first region of the alimentary canal and a second magnetic member 320 in a second region of the alimentary canal can result in joining of the tissue of the first region of the alimentary canal with tissue of the second region of the alimentary canal (e.g., the formation of an anastomosis joining a first and second region of the alimentary canal. The joining of tissue of the first region of the alimentary canal with tissue of the second region of the alimentary canal typically includes a side-to-side anastomosis, although other types of anastomoses can be formed, such as end-to-side anastomosis, or an end-to-end anastomosis, for example.

The formation of the anastomosis can occur over a time within a range from about three days to 14 days, from about 4 days to 10 days, or from about 5 days to about 10 days, for example. This amount of time is sufficient to allow necrosis of tissue and for the tissue from the first target region to fuse with the tissue from the second target region. The thickness of a tissue disposed between a first magnetic member 310 and a second magnetic member 320 (e.g., an engaged magnetic member pair) can decrease over time. The tissue disposed between the magnetic members of a magnetic member pair 330 can completely necrotize or otherwise deteriorate, and, in some cases, this can cause the magnetic members of a magnetic member pair 330 to contact one another and eventually pass through the anastomosis and into the lumen.

Figure 5D:
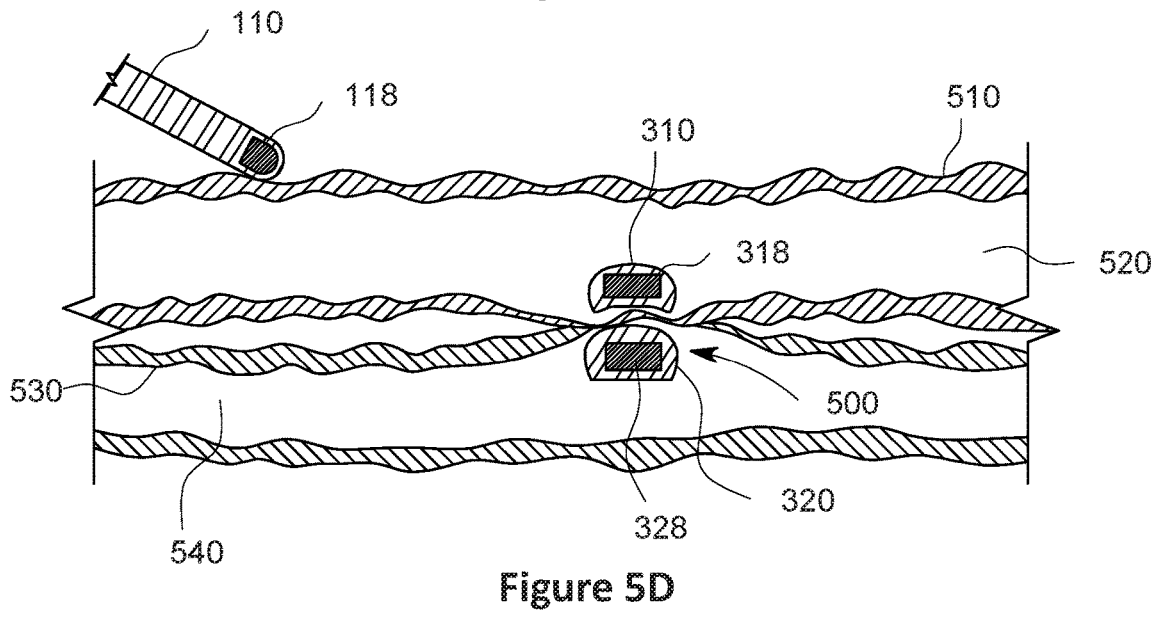
FIG. 5D shows a step of the disengaging and retracting a placement instrument following engaging of a first magnetic member with a second magnetic member, in accordance with some implementations.

FIG. 5D shows disengagement and retraction of placement instrument 110 from a magnetic member pair. The placement instrument 110 can be disengaged from a magnetic member and/or retracted from the region in which the first magnetic member 310 is engaged with the second magnetic member 320 without dislodging the first magnetic member 310 from the second magnetic member 320. The magnetic material, shape, or size of the placement instrument 110 can be designed to facilitate retraction of the placement instrument without dislodging the individual magnetic members of an engaged or assembled magnetic member pair. The placement instrument 110 may include a magnetic material 118 configured to produce a weaker magnetic field than the magnetic member pair, thereby decreasing the interactive force of the placement instrument with the magnetic member and facilitating disengagement and retraction of the magnetic member without disengaging the assembled magnetic member pair 330.

The placement instrument 110 can also be used to retrieve a magnetic member (e.g., a first magnetic member 310 or a second magnetic member 320) or magnetic member pair 330 from the body, for example if placement of the magnets does not go as planned.

Formation of Anastomosis Using Magnetic Members and a Plurality of Placement Instruments FIGS. 6A-6C show a method of placing magnetic members using a plurality of placement instruments to generate an anastomosis between two regions of the body.

FIG. 6A shows the first placement instrument 110 engaging the first magnetic member 310, and the second placement instrument 140 engaging the second magnetic member 320. The first placement instrument 110 can be advanced within the patient so as to engage the first magnetic member 310. The second placement instrument 140 can be advanced within the patient so as to engage the second magnetic member 320 through the luminal wall. The second placement instrument 140 typically includes structures and configurations similar to the first placement instrument 110. A portion of tissue can be disposed between the first placement instrument 110 and the first magnetic member 310 as described herein. The second placement instrument 140 can engage the second magnetic member 320 similarly to that described herein with reference to first placement instrument 110 and first magnetic member 310, and the pressures, forces and methods of placement and manipulation can also be similar.

While the first placement instrument 110 engages the first magnetic member 310 across the luminal wall, the first magnetic member can be slid a distance along the gastrointestinal tract to a first target region. The first magnetic member can be slid along the luminal wall 510 while a second placement instrument engages the second magnetic member 320 across a second portion of tissue (e.g., luminal wall 540). The second magnetic member can be held in place at a second target region with the second placement instrument when the first placement instrument 110 moves the first magnetic member 310 to the first target location, as depicted in FIG. 6A. The method can further include sliding the second placement instrument 140, which is engaged with a second magnetic member across a second portion of tissue, along the length of the gastrointestinal tract to the second target region, which can be done prior to, during or after, the first magnetic member has been placed at the first target location.

The first and second placement instruments can be configured in many ways as described herein in order to engage the first magnetic member and the second magnetic member. For example, the first and second placement instrument can each include a magnetic material near the distal end as described herein. The magnetic material may include a substantially unmagnetized magnetic material, such that the placement instrument is substantially insensitive to the magnetic field orientation of the magnetic member. Alternatively or in combination, the first placement instrument and the second placement instrument may each include a magnet so as to orient the corresponding magnetic member. For example, the first placement instrument and the second placement instrument may include magnets with opposite orientations located near the distal end. The materials and orientations of the first placement instrument 110, the second placement instrument 140, the first magnetic member 310, and the second magnetic member 320 can be configured with magnetic fields to orient the first magnetic member and the second magnetic member. For example, the first placement instrument 110 may include a first magnetic field with North ("N") oriented proximally and south ("S") oriented distally, so as to engage the first magnetic member 310 away from the engagement surface 316, for example on a side opposite the first engagement surface 316. The second placement instrument 140 may include a first magnetic field with S oriented proximally and N oriented distally, so as to engage the second magnetic member 320 away from the second engagement surface 326, for example on a side opposite the second engagement surface 326.

When formed as a pair, the magnetic field of the first magnetic member 310 aligns with the magnetic field of a first magnetic member 310. For example S of the first magnetic member 310 can be oriented toward N of the second magnetic member 320. The first placement instrument 110 engages the first magnetic member 310 on the opposite side of its outer surface from the side of its engagement surface. The second placement instrument 140 engages the second magnetic member 320 on the opposite side of its outer surface from the side of its engagement surface 326, although many other orientations can be used. The first placement instrument 110, first magnetic member 310, second placement instrument 140, and second magnetic member 320 can be configured such that, while engaged by the first placement instrument 110 and the second placement instrument 140, respectively, the engagement surface (e.g., the first engagement surface 316) of the first magnetic member 310 will engage the engagement surface (e.g., the second engagement surface 326) of the second magnetic member 320 when they are brought into close proximity (as exemplified in FIG. 6B).

The second placement instrument 140 can be used to position and/or to manipulate the second magnetic member 320 concurrently or in sequence with the positioning and/or manipulation of the first magnetic member 310. For example, FIG. 6B shows an implementation of a step of a method 502 to place a first magnetic member 310 and second magnetic member 320 of a magnetic member pair using a first placement instrument 110 and a second placement instrument 140 such that the magnetic fields of the first and second magnetic members are aligned and such that the first and second magnetic members engage with one another, compressing a region of an inner wall of a first lumen 520 and a region of an inner wall of a second lumen 530 between them.

FIG. 6C shows disengaging the first and second placement instruments from the placed first and second magnetic members. The first and second placement instruments can be disengaged from the first and second magnetic members and retracted from the target region after the first and second magnetic members have engaged with one another without causing the first and second magnetic members to disengage from one another. The first and second magnetic members can subsequently form the anastomosis as described herein.

Although the above methods show examples of methods of forming anastomoses, a person of ordinary skill in the art will recognize many adaptations and variations. For example, the steps can be performed in any order. Some of the steps can be removed or repeated. The step of any method as described herein can be combined with the step of any other method as described herein. Further, any method described herein can be combined any structure or element as described herein unless contrary teaching are provided in the present disclosure.

Clinical Applications of Magnetic Member Pairs

Figure 7:
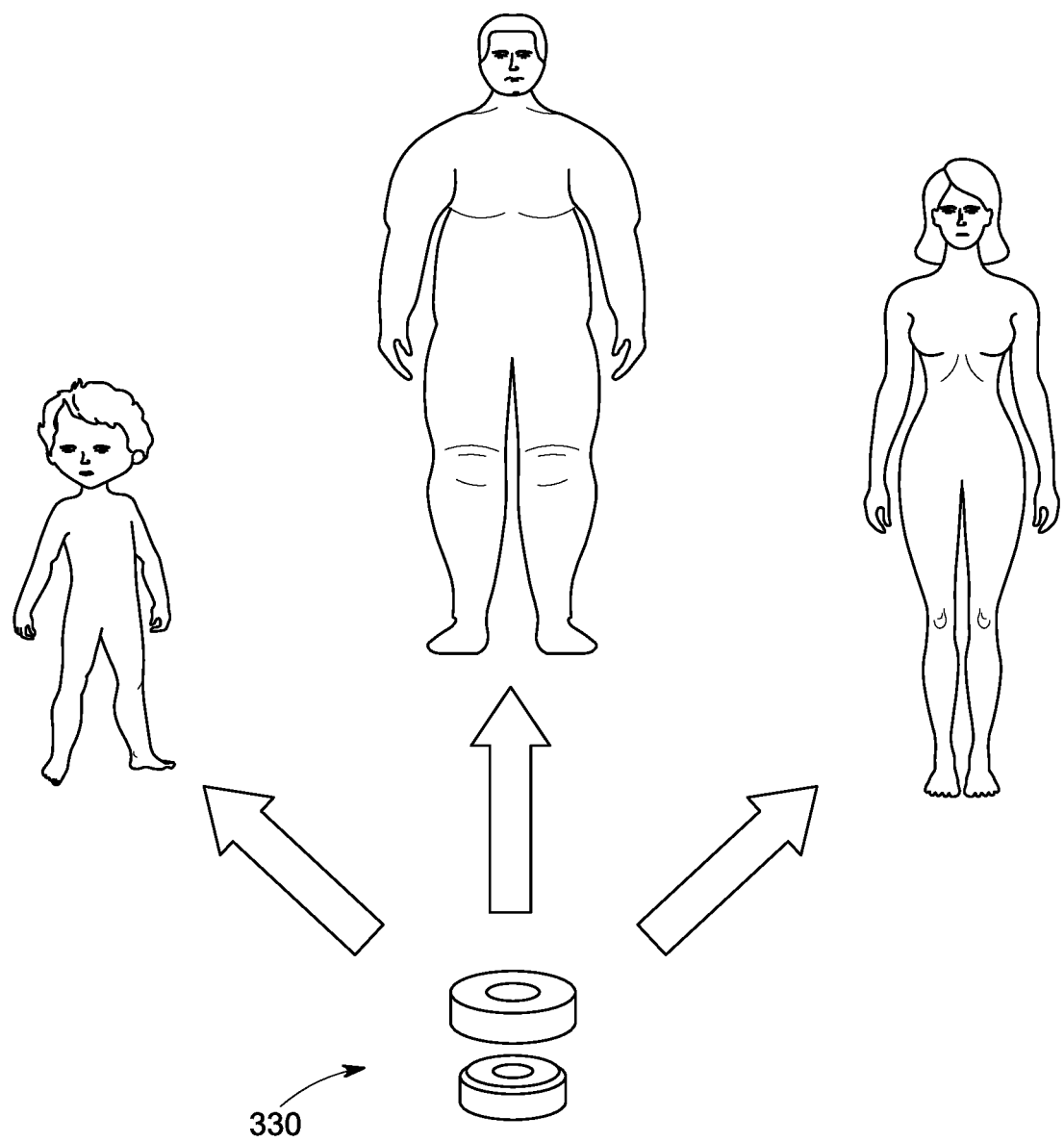
FIG. 7 shows a schematic diagram of the utility of a magnetic member pair configured for use with various types of patients, in accordance with some implementations.

As illustrated in the schematic diagram of FIG. 7, implementations of the devices, methods, and systems described herein can be applied to a wide range of different individuals (e.g., subjects or patients). A given magnetic member pair 330 can be used to form anastomoses in wide variety of patients having varying age, gender, height, weight, and ethnicity. Although the magnetic member pair can be selected based on characteristics and/or properties of the magnetic member pair 330 with respect to the expected function of the magnetic member pair 330 in creating an anastomosis in a particular patient, in many instances a single magnetic pair can be used to treat a wide variety of patients, which can simplify the procedure. However, if desired, a magnetic member pair 330 can be selected based on the strength of magnetic attractive force and/or the amount or spatial distribution of pressure generated between the first and second magnetic member of the magnetic member pair 330 when the first and second magnetic members are engaged with one another.

A target area in a first patient can include a different tissue thickness (e.g., luminal wall thickness, additional interstitial tissues such as visceral fat, etc.), different mechanical properties (e.g., different mechanical resistance to compression, different viscoelastic properties/kinetics, etc.), and/or different biological characteristics (e.g., rate of tissue remodeling during anastomosis formation, immune response to compressive force, etc.) than a corresponding anatomical target area in a second patient. The presently disclosed magnetic members are capable of treating such variability with a single configuration of the magnetic member pair, for example with a force greater than about 6N and the engagement surfaces as disclosed herein.

The particular surgical procedure may impact the selection of a magnetic member pair 330 (e.g., with regard to magnetic member size, shape, or magnetic properties). For example, pediatric patients may be treated with smaller magnetic members than adults.

A single magnetic member pair (e.g., having first and second magnetic members) can be configured to create an anastomosis in a wide range of patients, with target areas of various mechanical, biological, or physical properties, and for various procedures including the formation of an anastomosis with a magnetic member pair 330. The same first and second magnetic members can be used to create an anastomosis in a wide variety of patients, with target areas of various mechanical, biological, or physical properties, and for any procedure, in which the resulting anastomosis or anastomoses include similar or the same degrees of tissue remodeling, necrosis, or cutting. A single magnetic member pair can be configured to treat (e.g., to create an anastomosis in) an adult male patient or an adult female patient, for example. A single magnetic member pair can be configured to create an anastomosis in patients with a body mass index below about 15, from about 15 to about 18.5, from about 18.5 to about 25, from about 25 to about 30, or greater than about 30, for example.

The same magnetic member pair can be configured to create an anastomosis joining various target areas in the body. For example, the same magnetic member pair can be configured to create a side-to-side anastomosis between a first target area including a region of the duodenum and a second target area including a region of the small intestine near ileocecal valve and to create an end-to-side anastomosis between a first target area including a region of the small intestine and a second target area including a region of the stomach.

A single magnetic member pair 330 can be configured to create an anastomosis including treatment of different biological conditions. For example, the same magnetic member pair can be configured to create a Roux-en-Y gastric bypass or to create an anastomosis around a gastrointestinal blockage or in the treatment of a condition of the gastrointestinal tract related to diabetes, for example.

The amount of a luminal structure of the body that can be bypassed (e.g., a portion of the gastrointestinal tract such as the small intestine) can be from 10% to 90%, from 10% to 80%, from 10% to 70%, from 10% to 60%, from 10% to 50%, from 10% to 40%, from 10% to 30%, from 10% to 20% of the structure, or within a range defined by any two of the preceding values.

Figure 9A:
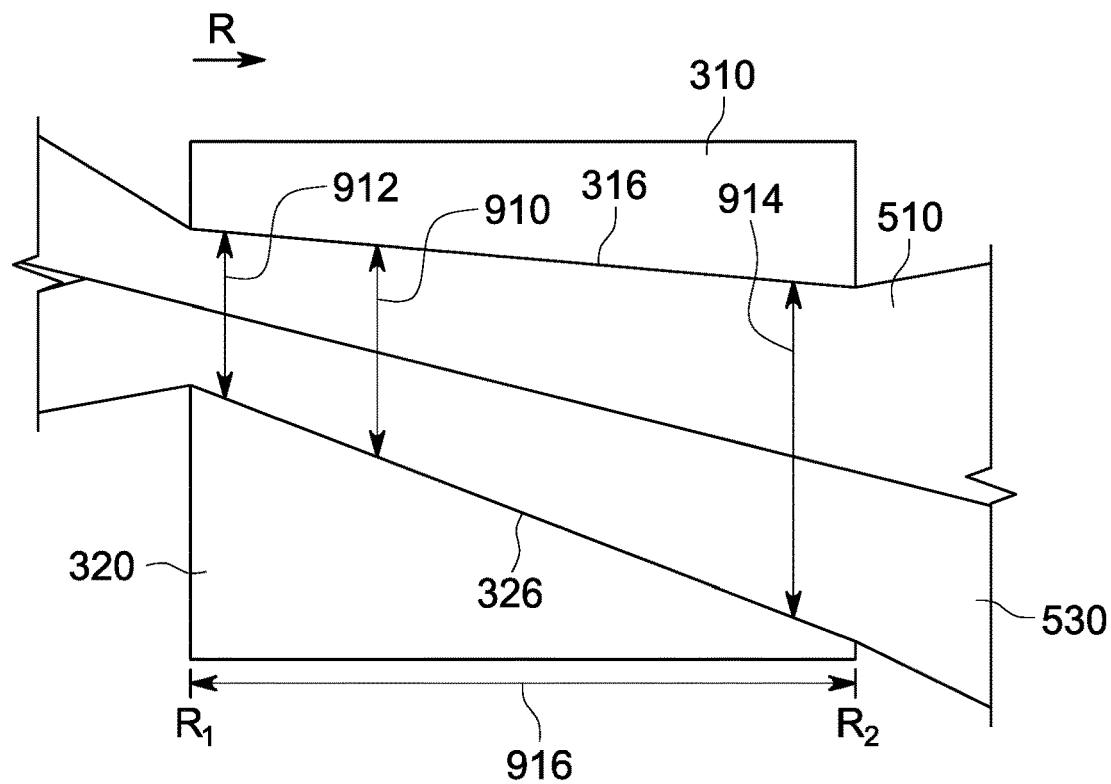
FIG. 9A shows tissue between engagement surfaces of first and second magnetic members, in accordance with some implementations.

FIG. 9A shows tissue between engagement surfaces 316, 326 of first and second magnetic members 310, 320, respectively. The engagement surfaces may include annular surfaces including an inner radial dimension R1 and an outer radial dimension R2, each defined with reference to a central axis of the respective magnetic member. The tissue may include first luminal wall tissue 510 and second luminal wall tissue 530. A separation distance 910 between the first engagement surface 316 and second engagement surface 326 can increase radially outward from R1 toward R2 from a first distance 912 at a first radially inward location to a second distance 914 at a second radially outward location, so as to generate a radial pressure gradient in the first luminal wall tissue and the second luminal wall tissue.

The first and second engagement surfaces can be shaped to provide a progressively increasing separation distance from the inner portion near R1 toward the outer portion near R2. The engagement surfaces can be shaped in many ways as described herein to provide this progressively increasing separation distance, for example with concave and convex surfaces as described herein. In general, the second surface includes a protruding surface and the first surface includes a recessed surface corresponding to the protrusion. Although reference is made to convex and concave spherical surfaces, the surfaces may include conic surfaces for example.

The first and second engagement surfaces can be shaped to provide a separation distance between the outer portions of the engagement surfaces when the inner portions of the engagement surfaces contact each other. For example, when the inner distance 912 near the inner location R1 is approximately zero due to contact between the engagement surfaces, the outer distance 914 includes a value dimensioned to provide an appropriate tissue pressure gradient, depending on the type of tissue. For example, contact separation distance of the outer portion may include a value of no more than about 5 mm, no more than about 4.5 mm, no more than about 4 mm, no more than about 3.5 mm, no more than about 3.0, no more than about 2.5 mm, no more than about 1.5 mm, no more than about 1 mm, no more than about 0.85 mm, no more than about 0.8 mm, no more than about 0.75 mm, no more than about 0.7 mm, no more than about 0.65 mm, no more than about 0.6 mm, no more than about 0.5 mm, no more than about 0.4 mm, no more than about 0.3 mm, or range defined by any two of the preceding values. For example, the distance can be within a range from about 0.65 to about 0.85 mm. The engagement surfaces may extend a radial distance 916. The first surface can be inclined relative to the second surface with an angle of inclination. The angle of inclination depends approximately on the radial distance 916 across which the engagement surfaces extend and the contact separation distance.

The distance 916 can be sized in many ways, and can be within a range defined by any two of the following values: 10 mm, 9 mm, 8 mm, 7 mm, 6 mm, 5.5 mm, 5.461 mm, 5 mm, 4.925 mm, 4.795 mm, 4.5 mm, 4 mm, 3.5 mm, 3 mm, 2.5 mm, or 2 mm.

Table I shows values of the angle of inclination for conic surfaces having a fixed radial distance 916 of 5.5 mm and varying contact separation distances. The edges of the conic surfaces can be rounded as described herein, so as to inhibit cutting of tissue and to allow the anastomosis to form over an appropriate amount of time as described herein. Spherical surfaces may include similar values and can be readily calculated by one of ordinary skill in the art based on the teachings provided herein. Although reference is made to spherical and conic surfaces, the surfaces can be shaped in many ways, for example, the inner portions of the engagement surfaces may include spherical surfaces and the outer portions of the engagement surfaces may include conic surfaces, for example. Also, the surfaces may include elliptical, sinusoidal or other shapes, for example.

TABLE 1

Relative Angles Inclination of Engagement Surfaces.

| | | | | | | |
|---|---|---|---|---|---|---|
| Pressure Gradient Distance (mm) (Radial Distance 916) | 5.5 | 5.5 | 5.5 | 5.5 | 5.5 | 5.5 |
| Separation Distance (mm) at Outer Edge | 0.5 | 0.6 | 0.7 | 0.8 | 0.9 | 1.0 |
| Percent Grade (Lower Engagement Surface Relative to Upper Engagement Surface) | 9.1 | 10.9 | 12.7 | 14.5 | 16.4 | 18.2 |
| Angle of Incline in Degrees (Lower Engagement Surface Relative to Upper Engagement Surface) | 5.2 | 6.2 | 7.2 | 8.3 | 9.3 | 10.3 |

The relative angles of inclination range from about 5.2 degrees to about 10.3 degrees for contact separation distances from 0.5 mm to about 1.0 mm. The percent grade of the separation distance can refer to the relative slope of the first surface relative to the second surface, for example when one of the surfaces includes a flat surface. The engagement surfaces can be shaped to have relative angles within a range defined by any two values shown in Table 1. Also, the angle of inclination may include a value within a range defined by any two of the following values in degrees 0, 0.5, 1.0, 2.0, 3.0, 4.0, 5.0, 6.0, 7.0, 8.0, 9.0, 10, 11, 12, 15, 30, 45, 60, 75. For curved surfaces or otherwise non-linear profile surfaces, the angle of inclination may increase non-linearly toward the outer region of the engagement surfaces; such curved or otherwise non-line profile surfaces may, if approximated by or averaged into a line (also referred to herein as an average radial cross-sectional profile), have similar angles of inclination.

Experiments conducted by the present inventors suggest that amounts of attractive force of at least 6N can be combined with the angles of inclination in order to provide anastomosis over an amount of time as described herein so as to form an anastomosis which heals two luminal walls together with healing, for example luminal walls of the stomach and small intestine, so as to safely form the anastomosis. In particular, the present inventors determined that magnetic member pairs that would initially produce pressure gradients on tissue clamped between them that ranged from 20 kPa to 80 kPa at the innermost diameter of the magnetic members and between 0 kPa and 15 kPa at the outermost diameter of the magnetic members (with between 2 mm to 10 mm of tissue interposed between them immediately after installation) were particularly effective at quickly generating high-quality anastomoses. The 20 kPa to 80 kPa is high enough pressure to cut off or restrict blood flow within the compression region so as to cause necrosis of the tissue within that region while being sufficiently low enough that immediate trauma, laceration, or other damage to the tissue is not caused by the magnetic member pair. Moreover, such initial pressures are also low enough to allow the engaged magnetic member pair to be repositioned, e.g., using a placement instrument or instruments, within the lumen or lumens prior to necrosis without tearing or otherwise damaging the tissue trapped between the magnetic members. At the same time, the pressure range of 0 kPa to 15 kPa is low enough that necrosis does not occur near the outer edge of the magnetic member pair, allowing the tissue trapped between the magnetic members towards the outer diameter of the magnetic members to fuse and/or heal together.

Of course, as the tissue encircled and clamped on by the highest-pressure annular region necrotizes, it will slowly decrease in thickness and thereby allow the magnetic members to move closer together and increase the magnetic attractive force generated between them. spreading the load radially outwards as the magnetic members gradually pull closer and closer together.

Figure 9B:
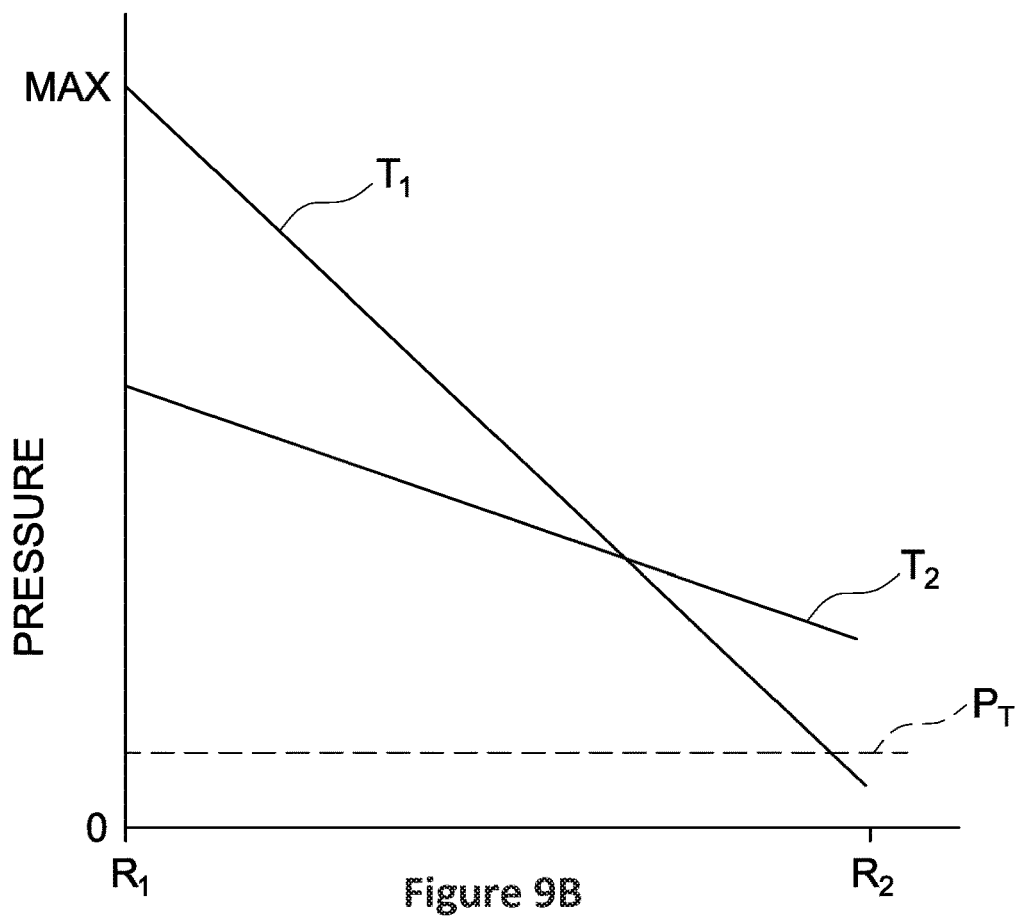
FIG. 9B shows tissue pressure gradient profiles at a first time prior to tissue necrosis and a second time subsequent to tissue necrosis for tissue compressed with first and second magnetic members as in FIG. 9A.

FIG. 9B shows tissue pressure gradient profiles at a first time T1 prior to tissue necrosis and a second time T2 subsequent to substantial tissue necrosis for tissue compressed with the first and second magnetic members as in FIG. 9A. Upon initial placement of the magnetic members, for example within a few minutes or an hour of placement, a maximum amount of pressure (MAX) is generated near the inner boundary of the engagement surfaces near R1. The maximum pressure can be within a range from about 20 kPa to about 80 kPa, for example. The amount of pressure at the outer portions of the engagement surfaces near R1 comprises a substantially smaller amount of pressure than the maximum pressure. The pressure near the outer portions of the engagement surfaces can be less than the threshold for necrosis PT. The amount of pressure to the tissue at the inner portion near R1 exceeds the pressure exerted on the outer portion near R2 by at least a factor of two, for example at least a factor of five. As tissue located in the inner portion near R1 necrosis, it weakens and allows the first engagement surface to move closer to the second engagement surface. This movement of the first engagement surface toward the second engagement surface increases the pressure on the outer portion of tissue near R2. As the necrosis continues and extends radially outward from tissue near R1, the pressure further increases on the tissue near R2, and eventually results in the pressure exceeding the threshold for necrosis PT. As the necrosis process continues, tissue necrosis beyond the outer boundary define by R2, and allows the first and second magnetic members to pass through the anastomosis. For example, with appropriately shaped engagement surfaces and amounts of force, the necrotized tissue can extend at least about one quarter mm or more beyond the outer boundary R2 in order to allow the magnetic member pair to pass through the formed anastomosis. For example, the necrotized tissue can pass through the anastomosis with the magnetic member pair an can extend a radial distance beyond the outer dimensions of the magnetic member pair by an amount within a range defined by any two of the following values 0.1 mm, 0.2 mm, 0.3 mm, 0.4 mm, 0.5 mm, 0.6 mm or 0.7 mm.

The engagement surfaces can be shaped and the amount of force can be configured to compress tissue with pressures above the necrosis threshold at locations radially beyond the engagement surfaces, for example beyond the outer dimension R2 of the engagement surfaces. For example, the engagement surfaces can be dimensioned so as to provide an appropriate contact separation distance at the outer portion so as to compress tissue when the tissue between the inner portions of the contact surfaces has necrotized. For example, small intestine tissue can include an uncompressed thickness within a range from about 2 mm to about 3 mm. Stomach tissue can include an uncompressed thickness within a range from about 4 mm to about 6 mm. The contact separation distance can be configured to provide sufficient compression to two portions of small intestinal tissue or to intestinal tissue compressed with stomach tissue, for example with a contact separation distance of about 2 mm.

While the first and second magnetic members can be configured in many ways, the inner portion may be configured to apply an initial pressure on luminal tissue within a range from about 20 to 80 kPa, and the outer portion may be configured to apply an initial pressure on luminal tissue within a range from about 2 kPa to about 12 kPa, for example. These pressure profiles can be provided with the forces between the magnetic members as described herein, for example at least about 6N. The radial distance over which the pressure gradient extends can be within a range from about 0.5 mm to about 8 mm, for example, and the pressure gradient may extend no more than about 8 mm, for example, no more than about 2 mm.

The engagement surfaces can be configured with appropriate separation distances so as to provide the pressure gradients as described herein. For example, the first engagement surface can be inclined relative to the second engagement surface as shown and described herein, e.g. with reference to FIGS. 3A-3G, 8 and 9A.

While preferred implementations of the present invention have been shown and described herein, it will be obvious to those skilled in the art that such implementations are provided by way of example only. Numerous variations, changes, and substitutions will now occur to those skilled in the art without departing from the invention. It should be understood that various alternatives to the implementations of the invention described herein may be employed in practicing the invention. It is intended that the following claims define the scope of the invention and that methods and structures within the scope of these claims and their equivalents be covered thereby. In addition to the claims appended to this specification, the following numbered implementations are also considered to be specifically within the scope of this disclosure, in addition to any implementations that are otherwise evident from the discussion previously in this disclosure. It will be understood that discussion of side-to-side anastomosis formation herein may also be relevant to end-to-end and side-to-end anastomosis formation (and vice-versa).

Implementation 1: A system for forming a side-to-side anastomosis in a gastrointestinal tract of a patient, the system including: a first magnetic member configured to be located adjacent a first luminal tissue region at a first location along the gastrointestinal tract; and a second magnetic member configured to be located adjacent a second luminal tissue region at a second location along the gastrointestinal tract wherein: the first and second magnetic members are configured to attract one another with a force of at least about 6 N when engaged with one another with the first and second luminal tissue regions interposed between them so as to bring together the first and second luminal tissue regions and effect necrosis in portions of the first and second luminal tissue regions while forming the anastomosis between the first and second luminal tissue regions, and the first and second magnetic members are configured to form a small intestine side-to-side anastomosis between a first small intestine location and a second small intestine location when the first magnetic member and the second magnetic members are, respectively, placed in the first small intestine location and the second small intestine location and caused to engage with one another and a small intestine-to-stomach anastomosis between a small intestine location and a stomach location when the first magnetic member and the second magnetic members are each placed in a different one of the small intestine location and the stomach location and caused to engage with one another.

Implementation 2: The system of implementation 1, wherein the first magnetic member includes a first engagement surface and the second magnetic member includes a second engagement surface inclined relative to the first engagement surface when magnetically aligned with the first magnetic member.

Implementation 3: The system of implementation 2 wherein the first engagement surface and the second engagement surface each have shape profiles dimensioned to provide a gap between portions of the first engagement surface and the second engagement surface that is within a range from about 0.65 mm to about 0.85 mm when other portions of the first engagement surface and the second engagement surface contact one another.

Implementation 4: The system of implementation 3, wherein the first engagement surface contacts the second engagement surface at inner locations near inner boundaries of the first and second engagement surfaces and wherein the gap exists between the first and second engagement surfaces near outer boundaries of the first and second engagement surfaces, and optionally wherein the first location is within about 0.25 mm of the inner boundaries and the second location is within about 0.25 mm of the outer boundaries.

Implementation 5: The system of implementation 1, wherein the first and second magnetic members are configured to generate a magnetic force of at least 6 N when spaced apart by a gap of about 2 mm to about 10 mm.

Implementation 6: The system of implementation 1, wherein the system is configured to form the anastomosis when installed in any individual from a plurality of different individuals.

Implementation 7: The system of implementation 1, wherein the small intestine location includes a duodenum of the patient.

Implementation 8: The system of implementation 1, wherein the first and second magnetic members are configured to attract one another with a force of no more than about 50 N when engaged with one another with the first and second luminal tissue regions interposed between them.

Implementation 9: The system of implementation 1, wherein the first and second magnetic members are configured to attract one another with a force within a range from about 10 N to about 50 N when engaged with one another with the first and second luminal tissue regions interposed between them.

Implementation 10: The system of implementation 1, wherein the first and second magnetic members are configured to attract one another with a force within a range from about 10 N to about 30 N when engaged with one another with the first and second luminal tissue regions interposed between them.

Implementation 11: The system of implementation 1, wherein the forced is distributed across a substantially flat surface area.

Implementation 12: A system for forming a side-to-side anastomosis in a gastrointestinal tract of a patient, the system including: a first magnetic member configured to be located adjacent a first luminal tissue region at a first location along the gastrointestinal tract; and a second magnetic member configured to be located adjacent a second luminal tissue region at a second location along the gastrointestinal tract, wherein: the first and second magnetic members are configured to attract one another and compress the first and second luminal tissue regions with a radial pressure gradient in portions of the first and second luminal tissue regions, so as to effect necrosis in portions of the first and second luminal tissue regions while forming the anastomosis between the first and second luminal tissue regions, and the pressure gradient provided by the portions of the first and second luminal tissue regions has a radially inwardly increasing pressure profile, and wherein pressure exerted on inner portions of the first and second luminal tissue regions is greater than pressure exerted on outer portions of the first and second luminal tissue regions by at least a factor of 2.

Implementation 13: The system of implementation 12, wherein pressure exerted on the inner portion is greater than pressure exerted on the outer portion by at least a factor of 5.

Implementation 14: The system of implementation 12, wherein the first and second magnetic members are configured such that within an hour of the first and second magnetic members having been attracted to each other with the first and second luminal tissue regions compressed therebetween, the pressure exerted on the inner portion is within a range from about 20 kPa to about 80 kPa and the pressure exerted on the outer portion is within a range from about 0 kPa to about 15 kPa.

Implementation 15: The system of implementation 12, wherein a difference between pressure exerted on the inner portions and pressure exerted on the outer portions decreases over time after the first and second magnetic members have been attracted to each other with the first and second luminal tissue regions compressed therebetween.

Implementation 16: The system of implementation 15, wherein pressure exerted on the outer portions increases over time after the first and second magnetic members have been attracted to each other with the first and second luminal tissue regions compressed therebetween.

Implementation 17: The system of implementation 12, wherein pressure initially exerted on the outer portions after the first and second magnetic members have been attracted to each other with the first and second luminal tissue regions compressed therebetween is below a threshold pressure to effect necrosis in portions of the first and second luminal tissue compressed between the outer portions.

Implementation 18: The system of implementation 17, wherein the threshold pressure is about 5 kPa.

Implementation 19: The system of implementation 17, wherein pressure exerted on the outer portions when the first and second magnetic members have been attracted to each other with the first and second luminal tissue regions compressed therebetween increases over time to above the threshold pressure in response to necrosis of portions of the first and second luminal tissue compressed between the inner portions.

Implementation 20: The system of implementation 12, wherein pressure initially exerted on the inner portions after the first and second magnetic members have been attracted to each other with the first and second luminal tissue regions compressed therebetween is above a threshold pressure to effect necrosis of portions of the first and second luminal tissue compressed between the inner portions.

Implementation 21: The system of implementation 12, wherein the pressure gradient extends across a radial length of no more than about 10 mm.

Implementation 22: The system of implementation 12, wherein the pressure gradient exists across a radial length of between about 2 mm to 10 mm.

Implementation 23: An instrument for guiding a first magnetic member to form an anastomosis, the instrument including: an elongate member having a distal portion and a proximal portion; and a magnetic material located on the distal portion of the elongate material, wherein the magnetic material is configured to engage to the first magnetic member with a force of no more than about 6N and guide the first magnetic member towards a target location for forming the anastomosis.

Implementation 24: The instrument of implementation 23, wherein the magnetic material is configured to engage with the first magnetic member with a luminal wall or walls interposed therebetween such that the instrument applies a pressure of no more than about 100 kPa to said luminal wall.

Implementation 25: The instrument of implementation 23, wherein the distal portion includes a rounded end to engage the first magnetic member with decreased pressure to tissue located between the magnetic material and the first magnetic member.

Implementation 26: A system that includes the of implementation 23, wherein the first magnetic member includes rounded edges to decrease pressure to a luminal wall when the first magnetic member moves along the luminal wall with engagement by the distal portion.

Implementation 27: The instrument of implementation 23, wherein the instrument is configured to facilitate guiding the first magnetic member along a luminal wall of a gastrointestinal tract of a patient towards the target location.

Implementation 28: The instrument of implementation 23, wherein the elongate member includes a flexible shaft.

Implementation 29: The instrument of implementation 23, wherein the elongate member includes a rigid shaft.

Implementation 30: The instrument of implementation 23, wherein the elongate member has a length of no more than about 50 cm.

Implementation 31: The instrument of implementation 23, further including a handle located on the proximal portion of the elongate member, wherein the handle is configured to be grasped by a user.

Implementation 32: The instrument of implementation 31, wherein the handle includes a shaft.

Implementation 33: The instrument of implementation 31, wherein the handle together with the elongate member has a length of no more than about 100 cm.

Implementation 34: The instrument of implementation 23, wherein the magnetic material includes a magnet.

Implementation 35: The instrument of implementation 34, wherein the magnetic material and the first magnetic member are configured to engage each other with an attractive magnetic force.

Implementation 36: The instrument of implementation 23, wherein the distal end of the instrument has a shape that is complementary to a shape of the first magnetic member.

Implementation 37: The instrument of implementation 23, wherein the instrument is configured to an attractive force between the magnetic material and the first magnetic member is less than an attractive force between the first magnetic member and a second magnetic member configured to form the anastomosis with the first magnetic member.

Implementation 38: The instrument of implementation 23, wherein the magnetic material is configured to engage to the first magnetic member with a force within a range from about 0.01 N to about 4 N.

Implementation 39: The instrument of implementation 23, wherein the magnetic material is configured to engage to the first magnetic member with a force within a range from about 0.1 N to about 2 N.

Implementation 40: The instrument of implementation 23, wherein the magnetic material is configured to engage to the first magnetic member with a pressure no more than about 50 kPa through a first luminal wall and a second luminal wall.

Implementation 41: The instrument of implementation 23, wherein a cross-sectional diameter of the instrument is no more than 12 mm.

Implementation 42: The instrument of implementation 23, wherein a cross-sectional diameter of the instrument is no more than 5 mm.

Implementation 43: The instrument of implementation 23, wherein a cross-sectional diameter of the elongate member is substantially fixed along a majority of the length of the elongate member.

Implementation 44: The instrument of implementation 23, wherein the instrument is configured to be slid through a gastrointestinal tract of a patient without incising a tissue of the patient. For example, edges of the instrument (or of the magnetic members, for that matter, in some implementations may be radiused to 2 mm or more, and the surfaces intended to contact the tissue may be smooth.

Implementation 45: The instrument of implementation 23, wherein the instrument is flexible and has a length of at least 1 meter.

Implementation 46: A system for forming an anastomosis, the system including the instrument of implementation 23; a first magnetic member configured to engage the magnetic material of the instrument; and a second magnetic member configured to attract the first magnetic member.

Implementation 47: The system of implementation 46, further including a second instrument for guiding the second magnetic member towards the target location near the first magnetic member.

Implementation 48: The system of implementation 47, wherein the second instrument includes: an elongate member having a distal portion and a proximal portion; and a magnetic material located on the distal portion of the elongate material, wherein the magnetic material is configured to engage to the second magnetic member with a force of no more than about 6N and guide the second magnetic member towards the location for forming the anastomosis.

Implementation 49: A method of placing a first magnetic member using the instrument of implementation 23, the method including: engaging the first magnetic member with the distal portion including the magnetic material; and guiding the first magnetic member to the target location with the distal portion.

Implementation 50: The method of implementation 49, further including disengaging the first magnetic member from the distal portion when a second magnetic member has been placed at a second target location adjacent to the target location with a first luminal wall and a second luminal wall interposed between the first magnetic member and the second magnetic member.

Implementation 51: The method of implementation 49, further including placing a second magnetic member at a second target location with a second instrument, the second instrument including a second distal portion including a second magnetic material.

Implementation 52: The method of implementation 51, further including separating the first instrument from the first magnetic member and the second instrument from the second magnetic member when the first magnetic member and the second magnetic member have been placed adjacent to each other with a first luminal wall and a second luminal wall interposed therebetween to form the anastomosis.

Implementation 53: The method of implementation 49, wherein guiding the first magnetic member includes sliding the instrument along an external surface of a gastrointestinal tract of a patient, thereby causing the first magnetic member to slide along an interior surface of the gastrointestinal tract of the patient, without incising a tissue of the patient.

Implementation 54: The method of implementation 53, wherein sliding the instrument along external surface of the gastrointestinal tract of the patient includes sliding the instrument a distance of at least 1 meter.

Implementation 55: The method of implementation 49, wherein engaging the first magnetic member with the distal portion includes contacting the first magnetic member with the distal portion.

Implementation 56: The method of implementation 49, wherein guiding the first magnetic member includes moving the first magnetic member with the distal portion together along an interior and exterior surface, respectively, of a gastrointestinal tract of a patient.

Implementation 57: A method of coupling magnetic members using the system of implementation 47, the method including: engaging the first magnetic member with the distal portion of the instrument; guiding the first magnetic member to the target location with the distal portion of the instrument; engaging the second magnetic member with the distal portion of the second instrument; guiding the second magnetic member to the target location with the distal portion of the second instrument; disengaging (1) the first magnetic member from the distal portion of the instrument and (2) the second magnetic member from the distal portion of the second instrument via, at least in part, an attractive force between the first magnetic member and the second magnetic member; and coupling the first magnetic member with the second magnetic member via the attractive force.

Implementation 58: The method of implementation 57, wherein the first magnetic member and the second magnetic member are separated by at least a tissue wall of a gastrointestinal tract of a patient.

Implementation 59: The method of implementation 57, wherein coupling the first magnetic member with the second magnetic member includes compressing a tissue wall of a gastrointestinal tract of a patient at the target location.

Implementation 60: A method of forming an anastomosis along an alimentary canal of a patient, the method including: selecting a pair of magnetic members from among a plurality of pairs of magnetic members to bypass a portion of material of the alimentary canal with the anastomosis, the plurality of pairs of magnetic members sized to form different sizes of anastomosis; delivering a first magnetic member of the pair of magnetic members to the alimentary canal of the patient; guiding the first magnetic member to a first target location within about 6 feet of the duodenum of the patient; and guiding a second magnetic member of the pair of magnetic members to a second target location within about six feet of the ileocecal valve of the patient, wherein the anastomosis forms between the first location and the second location with a size corresponding to the selected pair of magnetic members in order to bypass the alimentary canal between the first location and the second location.

Implementation 61: The method of implementation 60, wherein the portion is within a range from about 10 percent to 90 percent of contents passing through the bowel to be bypassed.

Implementation 62: The method of implementation 60, wherein the method is part of a bypass surgery that includes a bariatric surgery.

Implementation 63: The method of implementation 61, wherein the method is part of a bypass surgery to treat diabetes.

Implementation 64: The method of implementation 61, wherein the first magnetic member is delivered to the patient orally or rectally.

Implementation 65: The system, instrument, or method of any of the preceding implementations, wherein the first and second magnetic members have engagement surfaces with complementary shapes.

Implementation 66: The system, instrument, or method as in implementation 65, wherein the complementary shapes are configured to align the first magnetic member with the second magnetic member.

Implementation 67: The system, instrument, or method as in any of the preceding implementations, wherein the first magnetic members, the second magnetic members, or the first and second magnetic members have circular, oval, or polygonal shapes.

Implementation 68: The system, instrument, or method as in any of the preceding implementations, wherein an outer perimeter of the first magnetic member, the second magnetic member, or the first and second magnetic members have a circular, oval, or polygonal shape.

Implementation 69: The system, instrument, or method as in any of the preceding implementations, wherein the first magnetic member, the second magnetic member, or the first and second magnetic members have an inner opening that is circular, oval, or polygonal in shape.

Implementation 70: The system, instrument, or method as in any of the preceding implementations, wherein the first and second magnetic members have an annular shape.

Implementation 71: The system, instrument, or method as in any of the preceding implementations, wherein at least one of the first and second magnetic members has a flat engagement surface.

Implementation 72: The system, instrument, or method as in any of the preceding implementations, wherein at least one of the first and second magnetic members has a convex engagement surface.

Implementation 73: The system, instrument, or method as in implementation 72, wherein only one of the first and second magnetic members has the convex engagement surface and the other of the first and second magnetic members has a concave surface complementary to the convex surface.

Implementation 74: The system, instrument, or method as in any of the preceding implementations, wherein the first magnetic member has a first outer edge defined by a first outer diameter, and wherein the second magnetic member has a second outer edge defined by a second outer diameter.

Implementation 75: The system, instrument, or method as in implementation 74, wherein the first and second outer diameters are different.

Implementation 76: The system, instrument, or method as in implementation 74, wherein the first and second outer diameters are equal.

Implementation 77: The system, instrument, or method as in implementation 74, wherein each of the first and second outer diameters are within a range between about 8 mm and 30 mm.

Implementation 78: The system, instrument, or method as in implementation 74, wherein the first magnetic member further has a first inner edge defined by a first inner diameter and wherein the second magnetic member further has a second inner edge defined by a second inner diameter, and wherein the first and second magnetic members include an annulus.

Implementation 79: The system, instrument, or method as in implementation 78, wherein the first and second inner diameters are different.

Implementation 80: The system, instrument, or method as in implementation 78, wherein the first and second inner diameters are equal.

Implementation 81: The system, instrument, or method as in implementation 78, wherein a shortest length from the first inner edge to the first outer edge, or a shortest length from the second inner edge to the first outer edge, is within a range between about 1.5 mm and 8 mm.

Implementation 82: The system, instrument, or method as in any of the preceding implementations, wherein the first magnetic members, the second magnetic member, or the first and second magnetic members each have a maximum dimension equal to or less than about 25 mm.

Implementation 83: The system, instrument, or method as in any of the preceding implementations, wherein the first magnetic member, the second magnetic member, or the first and second magnetic members each have a maximum dimension equal to or less than about 15 mm.

Implementation 84: The system, instrument, or method as in any of the preceding implementations, wherein the first magnetic member, the second magnetic member, or the first and second magnetic members are configured to self-assemble inside the gastrointestinal tract of a patient.

Implementation 85: The system, instrument, or method as in any of the preceding implementations, wherein the first magnetic member includes a plurality of segments.

Implementation 86: The system, instrument, or method as in implementation 85, wherein the segments are movable relative to one another.

Implementation 87: The system, instrument, or method as in implementation 85, wherein the segments are transitionable between an assembled configuration for forming the anastomosis and an unassembled or collapsed narrow profile configuration sized for advancement along an endoscope.

Implementation 88: The system, instrument, or method as in implementation 85, wherein the second magnetic member includes a plurality of segments.

Implementation 89: The system, instrument, or method as in any of the preceding implementations, wherein the first and second magnetic members each have a casing that at least partially encloses the first and second magnetic members, respectively.

Implementation 90: The system, instrument, or method as in implementation 89, wherein each of the casings is made from a material selected from the group consisting of: PTFE, polycarbonate, biocompatible non-ferromagnetic material, and silicone.

Implementation 91: The system, instrument, or method as in implementation 89, wherein each of the casings defines an outer surface shape of the respective first and second magnetic members.

It should be understood that reference to "about," "approximately," "substantially," and the like herein may refer to values or ranges that are within ±10% of the indicated values or ranges, as well as to the actual value or range listed.

What is claimed is:

1. A system for forming a side-to-side anastomosis in a gastrointestinal tract of a patient, the system comprising:
    a first magnetic member configured to be located adjacent a first luminal tissue region at a first location along the gastrointestinal tract; and
    a second magnetic member configured to be located adjacent a second luminal tissue region at a second location along the gastrointestinal tract, the second luminal tissue region adjacent the first luminal tissue region, wherein:
        the first magnetic member comprises a first engagement surface and the second magnetic member comprises a second engagement surface inclined relative to the first engagement surface when magnetically aligned with the first magnetic member,
        the first engagement surface and the second engagement surface each have shape profiles dimensioned to provide a gap between portions of the first engagement surface and the second engagement surface that is within a range from about 0.65 mm to about 0.85 mm when other portions of the first engagement surface and the second engagement surface contact one another,
        the first and second magnetic members are configured to attract one another with a force of at least about 6 N when engaged with one another with the first and second luminal tissue regions interposed between them so as to bring together the first and second luminal tissue regions and effect necrosis in portions of the first and second luminal tissue regions while forming the anastomosis between the first and second luminal tissue regions, and the first and second magnetic members are configured to a) form a small intestine side-to-side anastomosis between a first small intestine location and a second small intestine location when the first magnetic member and the second magnetic members are, respectively, placed in the first small intestine location and the second small intestine location and caused to engage with one another and to b) form a small intestine-to-stomach anastomosis between a small intestine location and a stomach location when the first magnetic member and the second magnetic members are each placed in a different one of the small intestine location and the stomach location and caused to engage with one another.

2. The system of claim 1, wherein when the first engagement surface and the second engagement surface contact one another, the first engagement surface contacts the second engagement surface at inner locations near inner boundaries of the first and second engagement surfaces and wherein the gap exists between the first and second engagement surfaces near outer boundaries of the first and second engagement surfaces, and optionally wherein the first location is within about 0.25 mm of the inner boundaries and the second location is within about 0.25 mm of the outer boundaries.

3. The system of claim 1, wherein the first and second magnetic members are configured to form an anastomosis in the first and second luminal tissue regions when the first and second luminal tissue regions have a combined thickness within a range from about 4 mm to about 8 mm prior to compression and wherein the first and second magnetic members are configured to generate the anastomosis over a time within a range from about 3 days to 14 days for tissue within the range for the side-to-side small intestine-to-small intestine anastomosis and the small intestine-to-stomach anastomosis.

4. The system of claim 1, wherein the first magnetic member and the second magnetic member are configured to attract one another with a force of no more than about 50 N when engaged with one another with the first luminal tissue region and second luminal tissue region interposed between them.

5. The system of claim 1, wherein the first magnetic member and the second magnetic member are configured to attract one another with a force within a range from about 10 N to about 50 N when engaged with one another with the first luminal tissue region and second luminal tissue region interposed between them.

6. The system of claim 1, wherein the first magnetic member and the second magnetic member are configured to attract one another with a force within a range from about 10 N to about 30 N when engaged with one another with the first luminal tissue region and second luminal tissue region interposed between them.

7. The system of claim 1, wherein the force is distributed across a substantially flat surface area when the first magnetic member and the second magnetic member are magnetically engaged with one another with the first luminal tissue region and second luminal tissue region interposed between them.

8. The system of claim 1, wherein the first engagement surface and the second engagement surface have complementary shapes.

9. The system of claim 8, wherein the complementary shapes are configured to align the first magnetic member with the second magnetic member.

10. The system of claim 1, wherein the first magnetic member, the second magnetic member, or the first magnetic member and the second magnetic member has or have circular, oval, or polygonal shapes.

11. The system of claim 1, wherein an outer perimeter of the first magnetic member, an outer perimeter of the second magnetic member, or the outer perimeters of the first magnetic member and the second magnetic member has or have a circular, oval, or polygonal shape or shapes.

12. The system of claim 1, wherein the first magnetic member, the second magnetic member, or the first magnetic member and the second magnetic member has or have an inner opening that is circular, oval, or polygonal in shape.

13. The system of claim 1, wherein the first magnetic member and the second magnetic member both have an annular shape.

14. The system of claim 1, wherein at least one of the first engagement surface and the second engagement surface is flat.

15. The system of claim 1, wherein at least one of the first engagement surface and the second engagement surface is convex.

16. The system of claim 1, wherein the first engagement surface is convex and the second engagement surface is concave and complementary to the convex first engagement surface.

17. A system for forming a side-to-side anastomosis in a gastrointestinal tract of a patient, the system comprising:
a first magnetic member configured to be located adjacent a first luminal tissue region at a first location along the gastrointestinal tract; and
a second magnetic member configured to be located adjacent a second luminal tissue region at a second location along the gastrointestinal tract, wherein:
the first and second magnetic members are configured to attract one another and compress the first and second luminal tissue regions with a radial pressure gradient in portions of the first and second luminal tissue regions, so as to effect necrosis in portions of the first and second luminal tissue regions while forming the anastomosis between the first and second luminal tissue regions, the pressure gradient has a radially inwardly increasing pressure profile, and the pressure exerted on inner portions of the first and second luminal tissue regions is greater than pressure exerted on outer portions of the first and second luminal tissue regions by at least a factor of 2.

18. The system of claim 17, wherein the first and second magnetic members are configured to cause the pressure exerted on the inner portions to be greater than pressure exerted on the outer portions by at least a factor of 5 when the first and second magnetic members are attracted to one another with the first and second luminal tissue regions compressed therebetween.

19. The system of claim 17, wherein the first and second magnetic members are configured such that within an hour of the first and second magnetic members having been attracted to each other with the first and second luminal tissue regions compressed therebetween, the pressure exerted on the inner portions is within a range from about 25 kPa to about 53 kPa and the pressure exerted on the outer portions is within a range from about 2 kPa to about 12 kPa.

20. The system of claim 17, wherein pressure exerted on the outer portions when the first and second magnetic members have been attracted to each other with the first and second luminal tissue regions compressed therebetween increases over time to above a threshold pressure in response to necrosis of portions of the first and second luminal tissue compressed between the inner portions.

21. The system of claim 17, wherein pressure initially exerted on the inner portions after the first and second magnetic members have been attracted to each other with the first and second luminal tissue regions compressed therebetween is above a threshold pressure to effect necrosis of portions of the first and second luminal tissue compressed between the inner portions.

22. The system of claim 17, wherein the pressure gradient extends across a radial length of no more than about 8 mm.

23. The system of claim 17, wherein the pressure gradient exists across a radial length of no more than about 2 mm.

24. The system of claim 17, wherein a difference between pressure exerted on the inner portions and pressure exerted on the outer portions decreases over time after the first and second magnetic members have been attracted to each other with the first and second luminal tissue regions compressed therebetween.

25. The system of claim 24, wherein pressure exerted on the outer portions increases over time after the first and second magnetic members have been attracted to each other with the first and second luminal tissue regions compressed therebetween.

26. The system of claim 17, wherein pressure initially exerted on the outer portions after the first and second magnetic members have been attracted to each other with the first and second luminal tissue regions compressed therebetween is below a threshold pressure to effect necrosis in portions of the first and second luminal tissue compressed between the outer portions.

27. The system of claim 26, wherein the threshold pressure is about 5 kPa.

28. A method of forming an anastomosis along an alimentary canal of a patient, the method comprising:
    selecting a pair of magnetic members from among a plurality of pairs of magnetic members to bypass a portion of material with the anastomosis, the plurality of pairs of magnetic members sized to form different sizes of anastomosis;
    delivering a first magnetic member of the pair of magnetic members to the alimentary canal of the patient;
    guiding the first magnetic member to a first target location within about 6 feet of a duodenum of the patient; and
    guiding a second magnetic member of the pair of magnetic members to a second target location within about six feet of an ileocecal valve of the patient, wherein the anastomosis forms between the first location and the second location with a size corresponding to the selected pair of magnetic members in order to bypass the alimentary canal between the first location and the second location.

29. The method of claim 28, wherein the portion is within a range from about 10 percent to 90 percent of contents passing through a bowel of the patient to be bypassed.

30. The method of claim 29, wherein the first magnetic member is delivered to the patient orally or rectally.

31. The method of claim 28, wherein the method is part of a bypass surgery that comprises a bariatric surgery.

32. The method of claim 31, wherein the method is part of a bypass surgery to treat diabetes.

* * * * *